(12) United States Patent  (10) Patent No.: US 8,888,835 B2
Magnuson et al.  (45) Date of Patent: Nov. 18, 2014

(54) METHOD OF LOADING A MEDICAL DEVICE INTO A DELIVERY SYSTEM

(75) Inventors: Mark A. Magnuson, Bloomington, IN (US); James M. Carlson, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 800 days.

(21) Appl. No.: 12/989,025

(22) PCT Filed: Apr. 23, 2009

(86) PCT No.: PCT/US2009/002514
§ 371 (c)(1),
(2), (4) Date: Dec. 21, 2010

(87) PCT Pub. No.: WO2009/131689
PCT Pub. Date: Oct. 29, 2009

(65) Prior Publication Data
US 2011/0137398 A1 Jun. 9, 2011

Related U.S. Application Data

(60) Provisional application No. 61/047,371, filed on Apr. 23, 2008.

(51) Int. Cl.
*A61F 2/06* (2013.01)
*C22F 1/10* (2006.01)
*C22F 1/00* (2006.01)
*A61F 2/95* (2013.01)

(52) U.S. Cl.
CPC ... *A61F 2/95* (2013.01); *C22F 1/10* (2013.01); *A61F 2002/9522* (2013.01); *A61F 2210/0014* (2013.01); *C22F 1/00* (2013.01); *C22F 1/006* (2013.01); *A61F 2250/0042* (2013.01)
USPC .......................................... 623/1.11

(58) Field of Classification Search
USPC ............................................ 623/1.11
See application file for complete search history.

(56) References Cited

U.S. PATENT DOCUMENTS 4,435,229 A  3/1984  Johnson
4,503,569 A  3/1985  Dotter (Continued)

FOREIGN PATENT DOCUMENTS

EP  0411118 A1  2/1991
EP  1205743 A1  5/2002

(Continued)

OTHER PUBLICATIONS

Bataillard, L.; Bidaux, J.E.; Gotthardt, R. "Interaction Between Microstructure and Multiple-Step Transformation in Binary NiTi Alloys Using in-situ Transmission Electron Microscopy Observations," *Philosophical Magazine A*, 1998, 78(2), pp. 327-344.

(Continued)

*Primary Examiner* — Darwin Erezo
*Assistant Examiner* — Martin T Ton
(74) *Attorney, Agent, or Firm* — Brinks Gilson & Lione

(57) ABSTRACT

A method of loading a medical device into a delivery system includes providing a two-stage shape memory alloy at a temperature at which at least a portion of the alloy includes austenite. A stress which is sufficient to form R-phase from at least a portion of the austenite is applied to the medical device at the temperature. A delivery configuration of the medical device is obtained, and the medical device is loaded into a restraining member. Preferably, the delivery configuration of the medical device includes stress-induced R-phase.

18 Claims, 20 Drawing Sheets

(56) References Cited

U.S. PATENT DOCUMENTS

| | | | |
|---|---|---|---|
| 4,580,568 A | 4/1986 | Gianturco | |
| 4,655,771 A | 4/1987 | Wallstén | |
| 4,665,906 A | 5/1987 | Jervis | |
| 4,681,110 A | 7/1987 | Wiktor | |
| 4,707,196 A | 11/1987 | Honma et al. | |
| 4,743,251 A | 5/1988 | Barra | |
| 4,753,689 A | 6/1988 | Rizzo et al. | |
| 4,795,458 A | 1/1989 | Regan | |
| 4,881,981 A | 11/1989 | Thoma et al. | |
| 4,935,068 A | 6/1990 | Duerig | |
| 4,954,126 A | 9/1990 | Wallstén | |
| 4,984,581 A | 1/1991 | Stice | |
| 5,037,427 A | 8/1991 | Harada et al. | |
| 5,061,275 A | 10/1991 | Wallstén et al. | |
| 5,067,957 A | 11/1991 | Jervis | |
| 5,147,370 A | 9/1992 | McNamara et al. | |
| 5,190,546 A | 3/1993 | Jervis | |
| 5,197,978 A | 3/1993 | Hess | |
| 5,201,901 A | 4/1993 | Harada et al. | |
| 5,226,913 A | 7/1993 | Pinchuk | |
| 5,354,309 A | 10/1994 | Schnepp-Pesch et al. | |
| 5,395,390 A | 3/1995 | Simon et al. | |
| 5,405,377 A | 4/1995 | Cragg | |
| 5,466,242 A | 11/1995 | Mori | |
| 5,534,007 A | 7/1996 | St. Germain et al. | |
| 5,540,712 A | 7/1996 | Kleshinski et al. | |
| 5,540,713 A | 7/1996 | Schnepp-Pesch et al. | |
| 5,545,210 A | 8/1996 | Hess et al. | |
| 5,554,181 A | 9/1996 | Das | |
| 5,562,641 A | 10/1996 | Flomenblit et al. | |
| 5,562,725 A | 10/1996 | Schmitt et al. | |
| 5,562,728 A | 10/1996 | Lazarus et al. | |
| 5,575,818 A | 11/1996 | Pinchuk | |
| 5,597,378 A | 1/1997 | Jervis | |
| 5,601,593 A | 2/1997 | Freitag | |
| 5,624,508 A | 4/1997 | Flomenblit et al. | |
| 5,630,840 A | 5/1997 | Mayer | |
| 5,636,641 A | 6/1997 | Fariabi | |
| 5,637,089 A | 6/1997 | Abrams et al. | |
| 5,674,277 A | 10/1997 | Freitag | |
| 5,718,159 A | 2/1998 | Thompson | |
| 5,741,333 A | 4/1998 | Frid | |
| 5,758,562 A | 6/1998 | Thompson | |
| 5,782,741 A | 7/1998 | Bradshaw et al. | |
| 5,830,179 A | 11/1998 | Mikus et al. | |
| 5,836,066 A | 11/1998 | Ingram | |
| 5,840,387 A | 11/1998 | Berlowitz-Tarrant et al. | |
| 5,843,119 A | 12/1998 | Shmulewitz | |
| 5,846,247 A | 12/1998 | Unsworth et al. | |
| 5,851,217 A | 12/1998 | Wolff et al. | |
| 5,876,434 A | 3/1999 | Flomenblit et al. | |
| 5,882,444 A | 3/1999 | Flomenblit et al. | |
| 5,888,201 A | 3/1999 | Stinson et al. | |
| 5,928,217 A | 7/1999 | Mikus et al. | |
| 5,964,770 A | 10/1999 | Flomenblit et al. | |
| 6,042,605 A | 3/2000 | Martin et al. | |
| 6,042,606 A | 3/2000 | Frantzen | |
| 6,051,021 A | 4/2000 | Frid | |
| 6,139,536 A | 10/2000 | Mikus et al. | |
| 6,306,141 B1 | 10/2001 | Jervis | |
| 6,402,765 B1 | 6/2002 | Monassevitch et al. | |
| 6,416,544 B2 | 7/2002 | Sugita et al. | |
| 6,416,545 B1 | 7/2002 | Mikus et al. | |
| 6,427,712 B1* | 8/2002 | Ashurst | 137/62 |
| 6,451,047 B2* | 9/2002 | McCrea et al. | 623/1.13 |
| 6,540,849 B2 | 4/2003 | DiCarlo et al. | |
| 6,569,183 B1 | 5/2003 | Kim et al. | |
| 6,572,646 B1 | 6/2003 | Boylan et al. | |
| 6,626,937 B1 | 9/2003 | Cox | |
| 6,656,201 B2 | 12/2003 | Ferrera et al. | |
| 6,666,881 B1 | 12/2003 | Richter et al. | |
| 6,758,858 B2* | 7/2004 | McCrea et al. | 623/1.13 |
| 6,776,795 B2 | 8/2004 | Pelton | |
| 6,783,438 B2 | 8/2004 | Aloise et al. | |
| 6,896,684 B2 | 5/2005 | Monassevitch et al. | |
| 6,899,730 B1 | 5/2005 | Rivelli, Jr. | |
| 7,033,386 B2 | 4/2006 | Richter et al. | |
| 8,191,220 B2* | 6/2012 | Magnuson et al. | 29/405 |
| 2002/0151967 A1 | 10/2002 | Mikus et al. | |
| 2002/0177899 A1 | 11/2002 | Eum et al. | |
| 2003/0018343 A1 | 1/2003 | Mathis | |
| 2003/0199920 A1 | 10/2003 | Boylan et al. | |
| 2004/0176799 A1* | 9/2004 | Chanduszko et al. | 606/213 |
| 2004/0260377 A1 | 12/2004 | Flomenblit et al. | |
| 2005/0043757 A1 | 2/2005 | Arad et al. | |
| 2005/0154450 A1 | 7/2005 | Larson et al. | |
| 2005/0187612 A1 | 8/2005 | Edwin | |
| 2005/0198777 A1 | 9/2005 | Mabe | |
| 2007/0079494 A1 | 4/2007 | Serrano | |

FOREIGN PATENT DOCUMENTS

| | | |
|---|---|---|
| EP | 0744164 B1 | 9/2003 |
| EP | 1354566 A2 | 10/2003 |
| JP | 59-113165 | 6/1984 |
| WO | WO 92/19310 | 11/1992 |
| WO | WO 95/30385 | 11/1995 |
| WO | WO 95/31945 | 11/1995 |
| WO | WO 97/13475 | 4/1997 |
| WO | WO 97/21403 | 6/1997 |
| WO | WO 00/04846 | 2/2000 |
| WO | WO 2006/019943 A1 | 2/2006 |
| WO | WO 2006/086709 A1 | 8/2006 |
| WO | WO 2008/070130 A1 | 6/2008 |

OTHER PUBLICATIONS

Batalu, D.; Guoqiu, H.; Aloman, A.; Xiaoshan, L.; Zhihua, Z. "Determination of Some Mechanical Properties of TiNi (50.6 at.% Ni) Shape Memory Alloy Using Dynamic Mechanical Analysis and Tensile Tests," *Journal of Optoelectronics and Advanced Materials*, 2006, 8(2), pp. 694-698.

Besseghini, S.; Villa, E.; Passaretti, F.; Carcano, G. "Two Way Shape Memory Training in NiTi Shape Memory Alloys," *Presentation at E-MRS Fall Meeting 2005*, Symposium C, 2005, http://www.science24.com/paper/3739, 1 page.

Besseghini, S.; Villa, E.; Portman, J. "DMA Characterization of a Ni50.5at%Ti Shape Memory Alloys," *Int. J. Appl. Electr. and Mech.*, 2006, 23, pp. 33-38.

Cai, W.; Lu, X.L.; Zhao, L.C. "Damping Behavior of TiNi-Based Shape Memory Alloys," Materials Science and Engineering A, 2005, 394, pp. 78-82.

Carballo, M.; Pu, Z.J.; Wu, K.H. "Variation of Electrical Resistance and the Elastic Modulus of Shape Memory Alloys Under Different Loading and Temperature Conditions," *Journal of Intelligent Material Systems and Structures*, 1995, 6, pp. 557-565.

Cha, S-Y.; Jeong, S-Y.; Park, J.H.; Park, S.E.; Park, J.K.; Cho, C.R. "Thermodynamic and Structural Characterization of High- and Low-Temperature Nitinol," *J. of Korean Phys. Soc.*, 2006, 49, pp. S580-S583.

Chanduszko, A. "Determination of Nitinol Transition Temperatures Using a Dynamical Mechanical Analyzer," *SMST-2000: Proceedings of the International Conference on Shape Memory and Superelastic Technologies*, edited by Russel, S.M.; Pelton, A.R., Fremont, California, USA, 2001, pp. 375-381.

Chang, C-Y.; Vokoun, D.; Hu, C-T. "Two-Way Shape Memory Effect of NiTi Alloy Induced by Constraint Aging Treatment at Room Temperature," *Metallurgical and Materials Transactions A*, 2001, 32A, p. 1629.

Duerig, T.W. "Some Unsolved Aspects of Nitinol," *Materials Science and Engineering A*, 2006, 438-440, pp. 69-74.

Duerig, T. "Puzzler 2," *The SMST Newsletter*, 2006, www.asminternational.org/smst/newsletter/issue2.htm, 2 pages.

Duerig, T.; Tolomeo, D.E.; Wholey, M. "An Overview of Superelastic Stent Design," *Min Invas Ther & Allied Technol*, 2000, 9(3/4), pp. 235-246.

Eggeler, G.; Khalil-Allafi, J.; Gollerthan, S.; Somsen, C.; Schmahl, W.; Sheptyakov, D. "On the Effect of Aging on Martensitic Transformations in Ni-Rich NiTi Shape Memory Alloys," *Smart Mater. Struct.*, 2005, 14, p. S186-S191.

(56) References Cited

OTHER PUBLICATIONS

Funakubo, H. *Shape Memory Alloys*, Gordon and Breach Science Publishers S.A., New York, USA, 1987, pp. 194-200, 267-269.

Greiner, C.; Oppenheimer, S.M.; Dunand, D.C. "High Strength, Low Stiffness, Porous NiTi With Superelastic Properties," *Acta Biomaterialia*, 2005, 1, pp. 705-716.

Hwang, C.M.; Meichle, M.; Salamon, M.B.; Wayman, C.M. "Transformation Behaviour of a $Ti_{50}Ni_{47}Fe_3$ Alloy I. Premartensitic Phenomena and the Incommensurate Phase," *Philosophical Magazine A*, 1983, 47(1), 9-30.

Hwang, C.M.; Meichle, M.; Salamon, M.B.; Wayman, C.M. "Transformation Behaviour of a $Ti_{50}Ni_{47}Fe_3$ Alloy II. Subsequent Premartensitic Behaviour and the Commensurate Phase," *Philosophical Magazine A*, 1983, 47(1), 31-62.

Hwang, C.M.; Wayman, C.M. "Diffuse Electron Scattering from an Incommensurate Phase in a $Ti_{58.7}Ni_{37.5}Al_{3.8}$ Alloy," *Acta Metallurgica*, 1984, 32(1), pp. 183-187.

Imbeni, V.; Mehta, A.; Robertson, S.W.; Duerig, T.W.; Pelton, A.R; Ritchie, R.O. "On the Mechanical Behavior of Nitinol Under Multiaxial Loading Conditions and InSitu Synchrotron X-Ray," *SMST-2003: Proceedings of the International Conference on Shape Memory and Superelastic Technologies*, edited by A.R. Pelton, T.W. Duerig, SMST Society, Inc., Menlo Park, California, USA, 2004, pp. 267-276.

Khachin, V.N.; Gjunter, V.E.; Sivokha, V.P.; Savvinov, A.S. "Lattice Instability, Martensitic Transformations, Plasticity and Anelasticity of TiNi," *Proc. ICOMAT*, 1979, 79, pp. 474-479.

Khalil-Allafi, J.; Eggeler, G.; Schmahl W.W.; Sheptyakov, D. "Quantitative Phase Analysis in Microstructures Which Display Multiple Step Martensitic Transformations in Ni-rich NiTi Shape Memory Alloys," *Materials Science and Engineering A*, 2006, 438-440, pp. 593-596.

Khalil-Allafi, J.; Ren, X.; Eggeler, G. "The Mechanism of Multistage Martensitic Transformations in Aged Ni-Rich NiTi Shape Memory Alloys," *Acta. Mater.*, 2002, 50, pp. 793-803.

Kim, J.I.; Liu, Y.; Miyazaki, S. "Ageing-induced Two-Stage R-Phase Transformation in Ti-50.9at.%Ni," *Acta. Mater.*, 2004, 52, pp. 487-499.

Ling, H.C.; Kaplow, R. "Phase Transitions and Shape Memory in NiTi," *Met Trans A*, 1980, 11A, pp. 77-83.

Lukáš, P.; Šittner, P.; Neov, D.; Novák, V.; Lugovyy, D.; Tovar, M. "R-Phase Phenomena in Neutron Diffraction Investigations of Thermomechanically Loaded NiTi Polycrystals," *Mater. Sci. Forum*, 2002, 404-407, pp. 835-840.

Mazzolai, F.M.; Biscarini, A.; Coluzzi, B.; Mazzolai, G.; Villa, E.; Tuissi, A. "Low-Frequency Internal Friction of Hydrogen-Free and Hydrogen-Doped NiTi Alloys," *Acta Materialia*, 2007, 55, pp. 4243-4252.

Mehta, A.; Gong, X-Y.; Imbeni, V.; Pelton, A.R.; Ritchie, R.O. "Understanding the Deformation and Fracture of Nitinol Endovascular Stents Using in Situ Synchrotron X-Ray Microdiffraction," *Advanced Materials*, 2007, 19, pp. 1183-1186.

Mehta, A.; Imbeni, V.; Ritchie, R.O.; Duerig, T.W. "On the Electronic and Mechanical Instabilities in $Ni_{50.9}Ti_{49.1}$," *Materials Science and Engineering A*, 2004, 378, pp. 130-137.

Michutta, J.; Somsen, Ch.; Yawny, A.; Dlouhy, A.; Eggeler, G. "Elementary Martensitic Transformation Processes in Ni-rich NiTi Single Crystals with $Ni_4Ti_3$ Precipitates," *Acta Materialia*, 2006, 54, pp. 3525-3542.

Mihálcz, I. "Fundamental Characteristics and Design Method for Nickel-Titanium Shape Memory Alloy," *Periodica Polytechnica Ser. Mech. Eng.*, 2001, 45(1), pp. 75-86.

Miyazaki, S.; Kimura, S.; Otsuka, K. "Shape-Memory Effect and Pseudoelasticity Associated with the R-Phase Transition in Ti-50·5at. %Ni Single Crystals," *Philos. Mag. A*, 1988, 57(3), pp. 467-478.

Miyazaki, S.; Otsuka, K. "Mechanical Behaviour Associated with the Premartensitic Rhombohedral-Phase Transition in a $Ti_{50}Ni_{47}Fe_3$ Alloy," *Philosophical Magazines A*, 1984, 50(3), pp. 393-408.

Miyazaki, S.; Otsuka, K.; Wayman, C.M. "The Shape Memory Mechanism Associated with the Martensitic Transformation in Ti-Ni Alloys—II. Variant Coalescence and Shape Recovery," *Acta Metall.*, 1989, 37(7), pp. 1885-1890.

Miyazaki, S;. Wayman, C.M. "The R-Phase Transition and Associated Shape Memory Mechanism in Ti-Ni Single Crystals," *Acta metall.*, 1988, 36(1), pp. 181-192.

Ng, K.L.; Sun, Q.P. "Stress-Induced Phase Transformation and Detwinning in NiTi Polycrystalline Shape Memory Alloy Tubes," *Mechanics of Materials*, 2006, 38, pp. 41-56.

Novák, V.; Šittner, P. "Micromechanical Model Simulation of Thermomechanical Behaviors of NiTi Polycrystals Undergoing B2-R-B19' Transformation," *Proceedings of the International Conference on Shape Memory and Superelastic Techologies*, Oct. 3-7, 2004 in Baden-Baden, Germany, ASM International, Materials Park, OH, 2006, pp. 143-149.

Otsuka, K. "Introduction to the R-Phase Transition," *Engineering Aspects of Shape Memory Alloys*, edited by T.W. Duerig, Butterworth-Heinemann, Great Britain, 1990, pp. 36-45.

Otsuka, K.; Ren, X. "Martensitic Transformations in Nonferrous Shape Memory Alloys," *Mater. Sci. Eng. A*, 1999; A273-275, pp. 89-105.

Otsuka, K.; Ren, X. "Physical Metallurgy of Ti-Ni-Based Shape Memory Alloys," *Prog. Mater. Sci.*, 2005, 50, pp. 511-678.

Proft, J.L.; Melton, K.N.; Duerig, T.W. "Yield Drop and Snap Action in a Warm Worked Ni-Ti-Fe Alloy," *ICOMAT-86 (Jap. Inst. of Metals)*, 1986, pp. 742-747.

Saburi, T. "Ti-Ni Shape Memory Alloys," *Shape Memory Materials*, edited by K. Otsuka and C.M. Wayman, Cambridge University Press, New York, New York, USA, 1998, pp. 49-96.

Salamon, M.B.; Meichle, M.E.; Wayman, C.M. "Premartensitic Phases of $Ti_{50}Ni_{47}Fe_3$," *Phys. Rev. B*, 1985, 31(11), pp. 7306-7315.

Schmahl, W.; Bochum, R.U. "Crystal Structure Determination of $Ni_4Ti_4$ Precipitates and R-Phase in SM Alloys," *BENSC Experimental Report*, 2003, 1 page.

Schetky, L.M. "Shape Memory Alloys," *Kirk Othmer Encyclopedia of Chemical Technology*, 3rd Ed., John Wiley & Sons, Inc., Canada, 1982, vol. 20, pp. 726-736.

Schuster, A.; Voggenreiter, H.F.; Balch, D.K.; Dunand, D.C. "Synchrotron X-Ray Study of Texture in Cold-Worked-Memory NiTi-Wires," *Mat. Res. Soc. Symp. Proc.*, 2001, 678, pp. EE2.6.1-EE2.6.6.

Schuster, A.; Voggenreiter, H.F.; Dunand, D.C.; Eggeler, G. "A New Type of Intrinsic Two-Way Shape Memory Effect in Hooks of NiTi-Wires," *J. Phys. IV France*, 2003, 112, pp. 1177-1180.

Sitepu, H.; Schmahl, W.W.; Allafi, J.K.; Eggeler, G.; Dlouhy, A.; Toebbens, D.M.; Tovar, M. "Neutron Diffraction Phase Analysis During Thermal Cycling of a Ni-Rich NiTi Shape Memory Alloy Using the Rietveld Method," *Scripta Mater.*, 2002, 46, pp. 543-548.

Šittner, P.; Landa, M.; Lukáš, P.; Novák, V. "R-Phase Transformation Phenomena in Thermomechanically Loaded NiTi Polycrystals," *Mechanics of Materials*, 2006, 38, pp. 475-492.

Šittner, P.; Landa, M.; Sedlák, P.; Lukáš, P.; Novák, V. "On the Role of the R-Phase in Thermomechanical Behaviors of Commercial NiTi Wires," *Proceedings of the International Conference on Shape Memory and Superelastic Techologies*, Oct. 3-7, 2004 in Baden-Baden, Germany, ASM International, Materials Park, OH, 2006, pp. 29-36.

Šittner, P.; Lukáš, P.; Neov, D.; Lugovyy, D. "Martensitic Transformations in NiTi Polycrystals Investigated by In-Situ Neutron Diffraction," *Materials Science Forum*, 2003, 426-432, pp. 2315-2320.

Šittner, P.; Novák, V.; Landa, M.; Lukáš, P.; "Deformation Processes in Functional Materials Studied by in situ Neutron Diffraction and Ultrasonic Techniques," *Mater. Sci. Eng. A*, 2007, 462, pp. 12-22.

Šittner, P.; Sedlák, P.; Landa, M.; Novák, V.; Lukáš, P.; "In situ Experimental Evidence on R-Phase Related Deformation Processes in Activated NiTi Wires," *Mater. Sci. Eng. A*, 2006, A438-440, pp. 579-584.

Thayer, T.A.; Bagby, M.D.; Moore, R.N.; DeAngelis, R.J. "X-Ray Diffraction of Nitinol Orthodontic Arch Wires," *American Journal of Orthodontics and Dentofacial Orthopedics*, 1995, pp. 604-612.

Tobushi, H.; Yamada, S.; Hachisuka, T.; Ikai, A.; Tanaka, K. "Thermomechanical Properties Due to Martensitic and R-Phase

(56) References Cited

OTHER PUBLICATIONS

Transformations of TiNi Shape Memory Alloy Subjected to Cyclic Loadings," *Smart Mater. Struct.*, 1996, 5, pp. 788-795.

Todoroki, T.; Tamura, H. "Effect of Heat Treatment After Cold Working on the Phase Transformation in TiNi Alloy," *Trans. Japan Inst. Metals*, 1987, 28(2), pp. 83-94.

Tsoi, K.A. "Thermomechanical and Transformational Behaviour and Applications of Shape Memory Alloys and their Composites," *A Thesis Submitted for the Degree of Doctor of Philosophy at the School of Aerospace, Mechanical and Mechatronic Engineering University of Sydney*, 2002, Chapter 1, pp. 1-16 (17 pages with title page).

Uchil, J.; Mahesh, K.K.; Ganesh Kumara, K. "Calorimetric Study of the Effect of Linear Strain on the Shape Memory Properties of Nitinol," *Physica B*, 2001, 305, pp. 1-9.

Uchil, J.; Mahesh, K.K.; Ganesh Kumara, K. "Electrical Resistivity and Strain Recovery Studies on the Effect of Thermal Cycling Under Constant Stress on R-phase in NiTi Shape Memory Alloy," *Physica B*, 2002, 324, pp. 419-428.

Vaidyanathan, R.; Bourke, M.A.M.; Dunand, D.C. "An in situ Neutron Diffraction Mechanical Study of Superelastic NiTi and NiTi-TiC Composites," *J. Phys. IV France*, 2003, 112, pp. 823-826.

Vaidyanathan, R.; Bourke, M.A.M.; Dunand, D.C. "Analysis of Neutron Diffraction Spectra Acquired in Situ During Stress-Induced Transformations in Superelastic NiTi," *J. Appl. Phys.*, 1999, 86, 3020-3029.

Vaidyanathan, R.; Bourke, M.A.M.; Dunand, D.C. "Phase Fraction, Texture and Strain Evolution in Superelastic NiTi and NiTi-TiC Composites Investigated by Neutron Diffraction," *Acta. Mater.*, 1999, 47, pp. 3353-3366.

Vaidyanathan, R.; Bourke, M.A.M.; Dunand, D.C. "Texture, Strain, and Phase-Fraction Measurements During Mechanical Cycling in Superelastic NiTI," *Metall. Mat. Trans. A*, 2001, 32A, pp. 777-786.

Wayman, C.M. "Transformation, Self-Accommodation, Deformation and Shape Memory Behavior of NiTi Alloys," *Shape Memory Materials—Proceedings of the MRS International Meeting on Advanced Materials in 1988*, Materials Research Society, Pittsburgh, USA, 1989, 9, pp. 63-76.

Wayman, C.M.; Cornelis, I.; Shimizu, K. "Transformation Behavior and the Shape Memory in Thermally Cycled TiNi," *Scripta Metall.*, 1972, 6, pp. 115-122.

Wu, K.; Dalip, S.K.; Liu, Y.; Pu, Z. "Damping Characteristics of R-Phase NiTi Shape Memory Alloys," *SPIE*, 1995, 2441, pp. 139-148.

Zhang, X.; Sehitoglu, H. "Crystallography of the B2 → R → B19' Phase Transformations in NiTi," *Mater. Sci. Eng. A*, 2004, 374, pp. 292-302.

The International Search Report and Written Opinion for International Patent Application No. PCT/US2007/024932 dated May 8, 2008.

The International Search Report and Written Opinion for Inernational Patent Application No. PCT/US2009/002514 dated Jul. 21, 2009.

"Nitinol FAQ," *Memry Corporation*, 2006, 6 pages (http://www.memry.com/nitinolfaq/nitinolfaq.html).

"Setting Shapes in NiTi," *Johnson Matthey*, (printed from website) 2006, 1 page (http://www.jmmedical.com/html/setting_shapes.html).

"Shape Memory Alloy," *Wikipedia, the Free Encyclopedia*, (printed from website) 2006, 4 pages (http://en.wikipedia.org/wiki/Shape_memory_alloy).

"Standard Terminology for Nickel-Titanium Shape Memory Alloys," *American Society for Testing and Materials (ASTM) Standard F2005-05*, ASTM International, West Conshohocken, PA, 2005, 3 pages.

"Standard Test Method for Determination of Transformation Temperature of Nickel-Titanium Shape Memory Alloys by Bend and Free Recovery," *American Society for Testing and Materials (ASTM) Standard F2082-03*, ASTM International, West Conshohocken, PA, 2003. 7 pages.

"Standard Test Method for Determination of Transformation Temperature of Nickel-Titanium Shape Memory Alloys by Bend and Free Recovery," *American Society for Testing and Materials (ASTM) Standard F2082-06*, ASTM International, West Conshohocken, PA, 2006, 7 pages.

"Standard Test Method for Transformation Temperature of Nickel-Titanium Alloys by Thermal Analysis," *American Society for Testing and Materials (ASTM) Standard F200405*, ASTM International, West Conshohocken, PA, 2005, 4 pages.

"Transformation Temperature Hysteresis in NiTi Alloys, "*Johnson Matthey*, (printed from website) 2006, 2 pages (http://www.jmmedical.com/html/hysteresis.html).

"Using Nitinol Alloys,"*Johnson Matthey Engineering Reference*, 2004, 65 pages (www.jmmedical.com).

* cited by examiner

METHOD OF LOADING A MEDICAL DEVICE INTO A DELIVERY SYSTEM

RELATED APPLICATION

The present patent document is the National Stage of International Application No. PCT/US2009/002514, filed Apr. 23, 2009, which claims the benefit of the filing date under 35 U.S.C. §119(e) of Provisional U.S. Patent Application Ser. No. 61/047,371, filed Apr. 23, 2008, which is hereby incorporated by reference in its entirety.

TECHNICAL FIELD

The present disclosure relates generally to medical devices, and more particularly to a method of loading a medical device into a delivery system.

BACKGROUND

Stents are tubular support structures that are implanted into body vessels to treat blockages, occlusions, narrowing ailments and other problems that may restrict flow through the vessel. Numerous vessels throughout the vascular system, including peripheral arteries, such as the carotid, brachial, renal, iliac and femoral arteries, and other vessels, may benefit from treatment by a stent. Typically, stents are delivered into a vessel in a low-profile delivery configuration and then radially expanded at a treatment site to support the vessel wall. Balloon-expandable stents expand in response to the inflation of a balloon, whereas self-expanding stents deploy automatically when released from a delivery device.

Self-expanding stents are often fabricated from superelastic or shape memory alloys, such as Nitinol, which can "remember" and recover a previous shape. For example, a self-expanding stent may be engineered to remember and recover an expanded configuration after being delivered into a vessel in a compressed, low profile state. In the case of Nitinol alloys, the source of the shape recovery is generally understood to be a phase transformation between a lower temperature phase (martensite) and a higher temperature phase (austenite), which may be driven by an increase in temperature (shape memory effect) or by the removal of an applied stress (superelastic effect).

BRIEF SUMMARY

Described herein is a method of loading a medical device comprising a two-stage shape memory alloy into a delivery system that involves a stress-induced R-phase transformation. Also described is a delivery system including the medical device. The inventors have recognized that the R-phase of a two-stage shape memory alloy, which is generally avoided or ignored in the medical device community, may provide advantages for medical devices.

According to one embodiment of the method, a medical device comprising a two-stage shape memory alloy is provided at a temperature at which austenite is present in the alloy. A stress is applied to the medical device at the temperature, and the stress is sufficient to form R-phase from at least a portion of the austenite. A delivery configuration of the medical device is obtained, and the medical device is loaded into a restraining member. Preferably, the delivery configuration of the medical device includes stress-induced R-phase.

According to a second embodiment of the method, a medical device comprising a two-stage shape memory alloy is provided, where the alloy is at a temperature at which the alloy includes a parent phase that is not R-phase. R-phase is stress-induced from the parent phase in at least a portion of the alloy at the temperature. A delivery configuration of the medical device is obtained, and the medical device is loaded into a restraining member. Preferably, the delivery configuration of the medical device includes stress-induced R-phase.

The delivery system for the medical device includes a restraining member and a medical device including a two-stage shape memory alloy. The medical device is maintained in a delivery configuration by the restraining member, and the delivery configuration of the medical device includes stress-induced R-phase. Preferably, the stress-induced R-phase is present in the medical device in regions of maximum strain. It is also preferred that the delivery configuration of the medical device does not include stress-induced martensite.

DETAILED DESCRIPTION

A method of loading a medical device comprising a two-stage shape memory alloy into a delivery system that involves a stress-induced R-phase transformation is described in detail below. A delivery system comprising the medical device is also described. The inventors have recognized that the R-phase of a two-stage shape memory alloy, which is generally avoided or ignored in the medical device community, may provide advantages for medical devices.

Phase Transformations in Shape Memory Materials

Nickel-titanium shape memory materials reversibly transform between a lower temperature phase (martensite) and a higher temperature phase (austenite). Austenite is characteristically the stronger phase, and martensite may be deformed up to a recoverable strain of about 8%. Strain introduced in the alloy in the martensitic phase to achieve a shape change may be recovered upon completion of a reverse phase transformation to austenite, allowing the material to return to a previous shape. The forward and reverse phase transformations may be driven by the application and removal of stress (superelastic effect) and/or by a change in temperature (shape memory effect). For the purposes of this disclosure, the term "shape memory alloy" can be used interchangeably with the term "superelastic alloy" to refer to materials suitable for the present method.

Figure 1A:
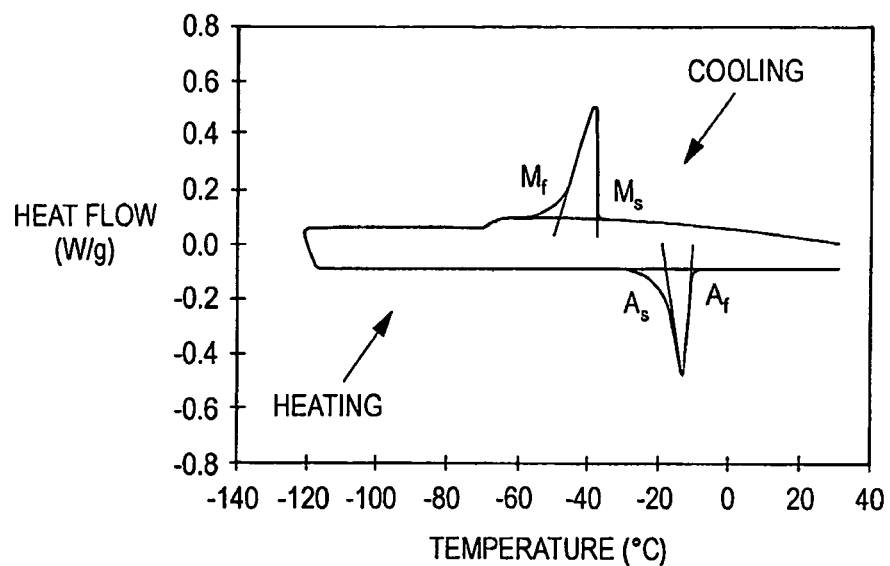
FIG. 1A is a differential scanning calorimetry (DSC) curve obtained for an exemplary nickel-titanium shape memory alloy exhibiting a single-stage transformation.

As generally understood by those skilled in the art, martensite start temperature ($M_s$) refers to the temperature at which a phase transformation to martensite begins upon cooling for a nickel-titanium shape memory alloy, and martensite finish temperature ($M_f$) refers to the temperature at which the phase transformation to martensite concludes. Austenite start temperature ($A_s$) refers to the temperature at which a phase transformation to austenite begins upon heating for a nickel-titanium shape memory alloy, and austenite finish temperature ($A_f$) refers to the temperature at which the phase transformation to austenite concludes. FIG. 1A shows differential scanning calorimetry (DSC) data for an exemplary nickel-titanium shape memory alloy that undergoes a single-stage transformation involving the austenitic and martensitic phases. The exemplary DSC data shown in the figure are based on those published in the ASTM standard F2005-05 and are not intended to be limiting. DSC data show the heat absorbed or released by a specimen as a function of temperature, and thus allow phase transformation temperatures to be identified. As shown, the relationship of the phase transformation temperatures for the exemplary shape memory alloy shown in FIG. 1A is $M_f < M_s < A_s < A_f$.

Some nickel-titanium shape memory alloys exhibit a two-stage transformation which includes a transformation to a rhombohedral phase (R-phase) in addition to the monoclinic (B19) martensitic phase and the cubic (B2) austenitic phase. The transformation to R-phase in two-stage shape memory materials occurs prior to the martensitic transformation upon cooling and prior to the austenitic transformation upon heating.

Figure 1B:
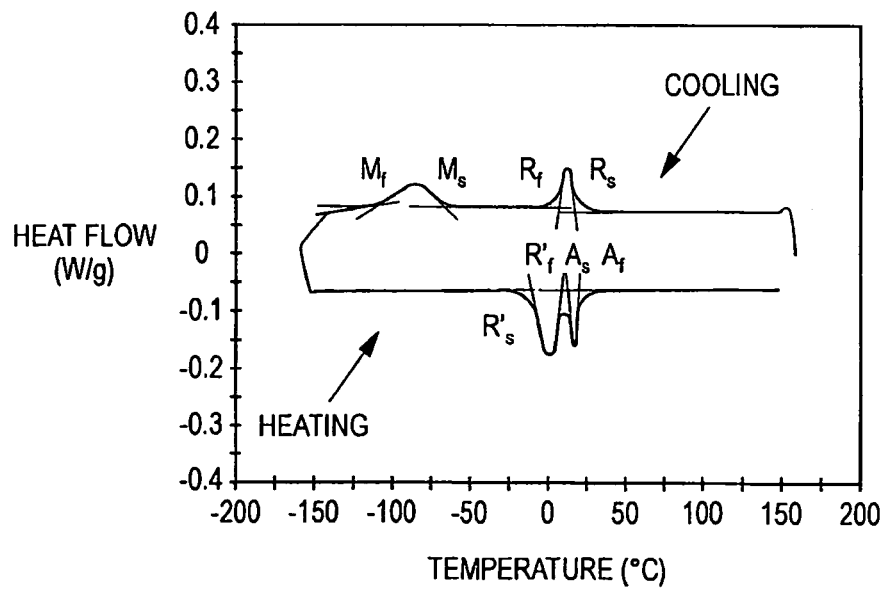
FIG. 1B is a differential scanning calorimetry (DSC) curve obtained for an exemplary nickel-titanium shape memory alloy exhibiting a two-stage transformation.

FIG. 1B shows a DSC plot of an exemplary shape memory alloy that undergoes a two-stage transformation. FIG. 1B is based on data published in the ASTM standard F2005-05 and is intended to be exemplary but not limiting. Referring to the figure, R'-phase start temperature ($R'_s$) is the temperature at which a phase transformation to R-phase begins upon heating for the two-stage shape memory material, and R'-phase finish temperature ($R'_f$) is the temperature at which the phase transformation to R-phase concludes upon heating. Note that, upon heating, the shape memory material may consist partly of the R-phase and partly of martensite from the R'-phase start temperature $R'_s$ until the R'-phase finish temperature $R'_f$, and then entirely of the R-phase from $R'_f$ until $A_s$ is reached, at which point the austenitic phase begins to form in the alloy. At or above $A_s$, the alloy may consist partly of R-phase and partly of austenite until $A_f$ is reached, at which point the alloy is entirely austenitic. The above assumes the exemplary shape memory alloy has a value of $R'_f$ which is below $A_s$. In practice, this may not always be the case.

The preceding discussion assumes the warming of the shape memory alloy occurs without an applied stress. If stress is applied to the alloy, the R-phase may remain stable at temperatures at or above $A_f$. As is generally understood to those of skill in the art, a phase that forms due to the application of stress to the alloy may be referred to as a "stress-induced" phase, while a phase that forms due to a change in temperature is typically referred to as a "thermally-induced" phase.

Again referring to FIG. 1B, R-phase start temperature ($R_s$) refers to the temperature at which a phase transformation to R-phase begins upon cooling for a two-stage shape memory material, and R-phase finish temperature ($R_f$) refers to the temperature at which the phase transformation to R-phase concludes upon cooling. Note that, upon cooling, the shape memory alloy may consist partly of the R-phase and partly of austenite from the R-phase start temperature $R_s$ until a temperature of $R_f$, and then entirely of the R-phase from $R_f$ until $M_s$ is reached, at which point the martensitic phase begins to form in the alloy. At or below a temperature of $M_s$, the alloy may consist partly of R-phase and partly of martensite until $M_f$ is reached, at which point the alloy is entirely martensitic. Again, this discussion assumes the cooling of the shape memory alloy occurs without an applied stress. If stress is applied to the alloy, the R-phase may appear at a temperature above $R_s$, and the R-phase transformation may conclude at a temperature above $R_f$. Similarly, under an applied stress, martensite may form at a temperature above $M_s$, and the transformation to martensite may conclude at a temperature above $M_f$.

Loading Method

Figure 2:
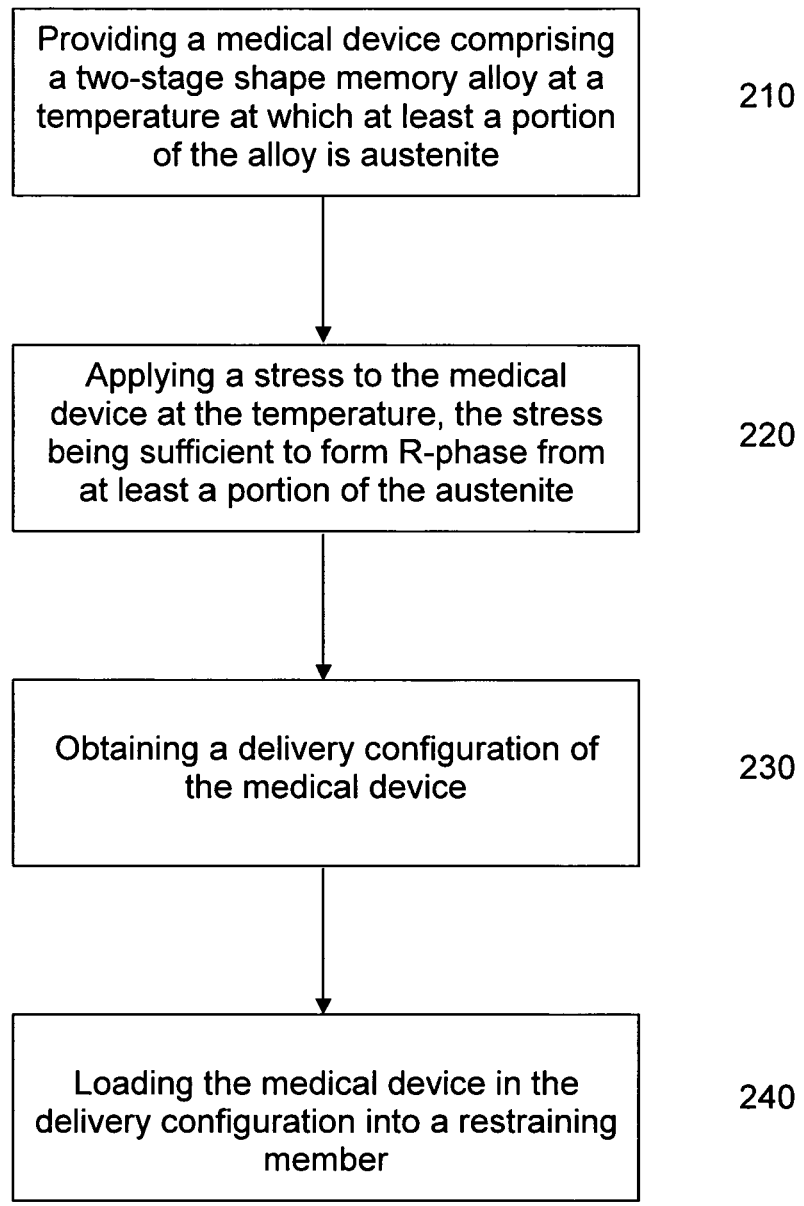
FIG. 2 is a flow chart illustrating the present method according to one embodiment.

Referring to the flow chart of FIG. 2, which shows one embodiment of the method to load a medical device into a delivery system, a medical device comprising a two-stage shape memory alloy is provided 210 at a temperature at which at least a portion of the alloy is austenite. A stress is applied 220 to the medical device at the temperature, and the stress is sufficient to form R-phase from at least a portion of the austenite. A delivery configuration of the medical device is obtained 230, and the medical device in the delivery configuration is loaded 240 into a restraining member. Preferably, the medical device comprises stress-induced R-phase in the delivery configuration.

The stress applied to the medical device may also be sufficient to form martensite from at least a portion of the R-phase that forms from the austenite, according to one embodiment. The stress may be sufficient to transform substantially all of the R-phase to martensite. Accordingly, the delivery configuration of the medical device may include stress-induced martensite in addition to or instead of stress-induced R-phase.

Alternatively, and preferably, the stress applied to the medical device is insufficient to form martensite from the R-phase. The stress is, however, sufficient to obtain a delivery configuration of the medical device. According to this embodiment, stress-induced martensite is not present in the delivery configuration of the medical device.

It is generally known that martensite can be stress-induced in a typical superelastic nickel-titanium alloy at a stress of about 350 MPa. In addition, the inventors have calculated the maximum stress to which an exemplary Zilver® stent (Cook Inc., Bloomington, Ind.) is exposed under typical compression forces. The analysis was based on an exemplary 140-mm long stent including 50 cells, with 27 apexes (connection points between adjacent struts) per cell. It was assumed that the stent was compressed to a delivery configuration using 4 $lb_f$. Per apex, the force was estimated to be 0.004 $lb_f$. Considering the dimensions of the apex, values of stress in the apex region ranging from about 19 to 76 MPa were calculated.

These values suggest that martensite may not be stress-induced in the stents during compression. Consistent with these figures, the stress applied to the medical device in the present method preferably does not exceed about 200 MPa. The stress may also not exceed 100 MPa.

It is also known in the art that the phase transformation temperatures of shape memory alloys can be altered by the processing history and/or composition of the shape memory alloy. For example, a nickel-rich Nitinol alloy (e.g., 51 at. % Ni, 49 at. % Ti) may have $A_f$ temperature below body temperature (37° C.), while an equiatomic Nitinol alloy (50 at. % Ni, 50 at. % Ti) may have an $A_f$ temperature of 100° C. or higher. Heat treatments and cold work may also impact the transformation temperatures.

The inventors believe that the stress required to stress-induce a particular phase from a parent phase is related to the transformation temperatures of that phase relative to the transformation temperatures of the parent phase. In particular, the inventors have recognized that, by appropriately processing the alloy to manipulate the phase transformation temperatures, it may be possible to alter the stress levels required to form the phases of interest. For example, a nickel-titanium alloy may be processed such that the temperature required to form martensite in the alloy ($M_s$) is significantly reduced compared to the temperature needed to form the R-phase ($R_s$). Correspondingly, the stress required to form (or stress-induce) martensite from the R-phase may be increased. As a result, a higher level of stress may be applied to the processed Ni—Ti alloy to deform the alloy and stress-induce the R-phase without stress-inducing martensite.

It is therefore contemplated, according to one embodiment of the method, that the shape memory alloy may be processed to maximize the difference between phase transformation temperatures so as to suppress the formation of one of the phases relative to the other. In other words, the alloy can be engineered such that more substantial differences in temperature and stress are needed to form a given phase from the parent phase. For example, as described above, the difference between the martensite start temperature ($M_s$) and the R-phase start temperature ($R_s$) of the alloy may be maximized to increase the stress required to form R-phase from martensite. In practice, this may be done by controlling the processing history (e.g., cold work, heat treatments) and/or composition (e.g., the presence and amount of any alloying elements) of the shape memory alloy.

By way of example, a self-expanding stent comprising a two-stage nickel-titanium shape memory alloy may be loaded into a transfer tube according to the following procedure. First, the stent may be maintained at or heated to a first temperature at or above the austenite start temperature $A_s$ of the shape memory alloy. At such a temperature, it is expected that the structure of the stent includes both R-phase and austenite. For example, the stent may be heated to a first temperature between about $A_s$ and $A_s+10°$ C. The first temperature may also lie between about $A_s$ and $A_s+6°$ C., or between $A_s$ and $A_s+2°$ C. A typical spread between $A_s$ and $A_f$ may be about 10° C. to 20° C. The first temperature may also be above the $A_f$ of the shape memory alloy, in which case it is expected that the structure of the stent is substantially entirely austenite.

While at the first temperature, a compressive force may be applied to the stent to obtain a reduced diameter configuration (i.e., a delivery configuration) suitable for loading the stent into the transfer tube (or sheath or other delivery system). The compressive force is also sufficient to form R-phase from at least a portion of the austenite in the stent. Typically, a force in the range of from about 4 lbs to about 10 lbs is appropriate. Higher or lower forces may be employed depending on the magnitude of the first temperature, the size of the stent, and other factors. For example, a stent compressed at a first temperature above $A_f$ of the shape memory alloy may require a higher compression force than a stent compressed at a temperature of $A_s$ due to the larger proportion of austenite present in the former stent.

The compressive force may be applied to the stent by a compression unit, such as, for example, a stent rolling apparatus that includes a flexible sheet rolled to define a cylindrical opening or aperture into which a stent may be inserted and then compressed. Preferably, the sheet is made of or coated with a material having a low coefficient of friction. By applying a force to an end of the sheet with the stent inside the opening, the diameter of the opening may be decreased and the stent may be radially compressed within the sheet. The compression unit alternatively may take the form of a stent crimping (compression) apparatus that includes a plurality of contracting members disposed about a cylindrical aperture. The stent may be inserted into the aperture and then compressed as the relative motion of the contracting members reduces the size of the aperture. Such compression machines are commercially available from various manufacturers, such as, for example, Machine Solutions, Inc. (Flagstaff, Ariz.). Alternatively, other compression units, bending machines, presses, forges, or other metalworking equipment known in the art may be used to apply the stress to the stent. Once radially compressed, the stent may be removed from the compression unit and loaded directly into a transfer tube or delivery system.

The loading method is suitable for use with self-expanding stents of any size, and it is applicable to medical devices other than self-expanding stents. For example, the medical device may be a stone retrieval basket, a snare, or an embolic protection filter including one or more shape memory/superelastic components (e.g., wires). In another example, the medical device may be a superelastic fenestration ring which is used as a coupling device for a stent graft. The stent graft may include a self-expanding stent with a graft material attached to the stent.

Figure 3:
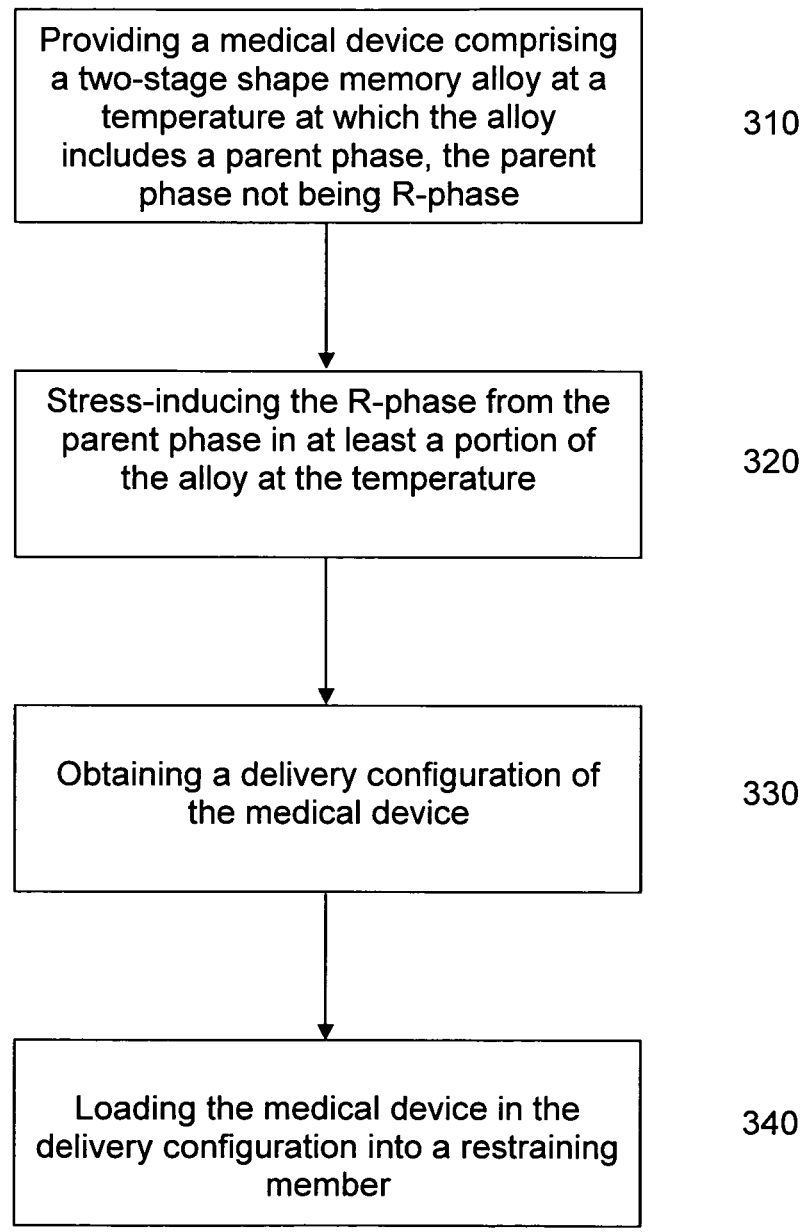
FIG. 3 is a flow chart illustrating the present method according to another embodiment.

The flow chart of FIG. 3 shows the method of loading a medical device into a delivery system according to another embodiment. The method entails providing 310 a medical device comprising a two-stage shape memory alloy, where the alloy is at a temperature at which the alloy includes a parent phase, the parent phase not being R-phase, and stress-inducing 320 the R-phase from the parent phase in at least a portion of the alloy at the temperature. A delivery configuration of the medical device is obtained, and the medical device is loaded into a restraining member. Preferably, the delivery configuration of the medical device includes stress-induced R-phase. Generally, the parent phase is austenite. Alternatively, the parent phase may be martensite.

The method illustrated in FIG. 3 may further entail stress-inducing martensite from the stress-induced R-phase. According to this embodiment, the delivery configuration of the medical device may include stress-induced martensite in addition to, or instead of, stress-induced R-phase. Preferably, however, the delivery configuration of the medical device does not include stress-induced martensite.

Delivery System for a Medical Device

Figure 4:
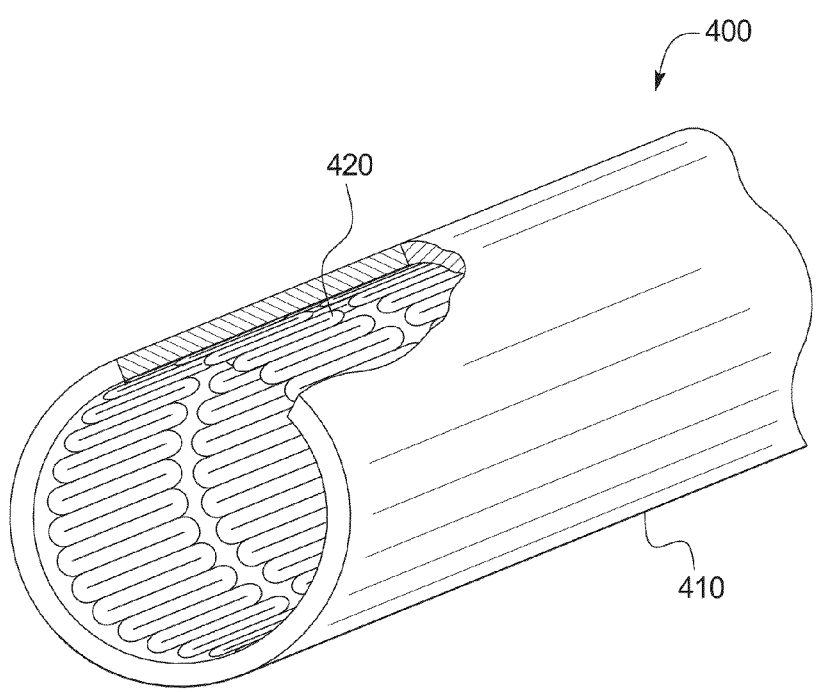
FIG. 4 is a partial cut-away view of an exemplary medical device in a delivery configuration within a delivery system.

Also described herein, and shown in FIG. 4 according to an exemplary embodiment, is a delivery system 400 for a medical device that includes a restraining member 410 and a medical device 420 including a two-stage shape memory alloy. The medical device 420 is maintained in a delivery configuration by the restraining member 410, and the delivery configuration includes stress-induced R-phase. According to this exemplary embodiment, the medical device 420 is a self-expanding stent and the restraining member 410 is a tubular sheath that overlies the stent. (A partial cut-away view of the sheath is shown in FIG. 4.) Preferably, the stress-induced R-phase is present in the delivery configuration of the medical device (e.g., stent) in regions of maximum strain (e.g. connection points or bends between adjacent struts). It is also preferred that the delivery configuration of the medical device does not include stress-induced martensite.

The medical device may alternatively be a stone retrieval basket, a snare, or an embolic protection filter including one or more shape memory/superelastic components (e.g., wires). In another example, the medical device may be a superelastic fenestration ring which is used as a coupling device for a stent graft. The stent graft may include a self-expanding stent with a graft material attached to the stent. The restraining member for these devices may be any low-profile component that can be delivered into a body vessel while maintaining the medical device in the delivery configuration.

The two-stage shape memory alloy employed in the medical device is preferably a nickel-titanium shape memory material (e.g., Nitinol) that undergoes an R-phase transformation. The nickel-titanium alloy may have a near-equiatomic composition. Such materials may be obtained from commercial sources or fabricated as described herein.

To produce the nickel-titanium shape memory alloy, the desired amounts of nickel and titanium may be melted and then cooled into an ingot or a workpiece. Melting methods known in the art, including but not limited to vacuum induction melting (VIM), vacuum consumable arc melting (VAR), and electron beam melting, may be employed to form the melt. Remelting is generally desirable to obtain satisfactory microstructural homogeneity in the ingot. For example, successive VAR processes or a VIM/VAR double melting process may be employed.

To ensure that the nickel-titanium alloy undergoes an R-phase transformation, it may be advantageous to select a nickel-rich composition, such as, for example, about 51 at. % Ni and 49 at. % Ti, for the melt. According to another aspect, one or more additional alloying elements (e.g., ternary or quaternary elements such as iron) may be included in the alloy composition. It may also be advantageous to cold work and then anneal the alloy at a temperature of between about 400° C. and 550° C., as will be described below. Each of these steps may help to suppress the martensitic phase transformation relative to the R-phase transformation.

The ingot formed from the melting process may be hot worked into a first shape by, for example, extruding, hot rolling, or forging. Hot working may be employed to break down the cast structure of the ingot and to improve mechanical properties. The hot working may be carried out at temperatures in the range of from about 700° C. to about 950° C. Preferably, the ingot undergoes a minimum deformation of about 90% during hot working in order to obtain a uniform microstructure.

The first shape may then be cold worked into a component by, for example, drawing or rolling. The cold working typically involves several passes in combination with interpass annealing treatments at temperatures in the range of from about 600° C. to about 800° C. The interpass annealing treatments soften the material between cold work passes, which typically impart 30-40% deformation to the material. Machining operations, such as, for example, drilling, cylindrical centerless grinding, or laser cutting may also be employed to fabricate the component.

A heat treatment may be employed to impart a "memory" of a desired high temperature shape and to optimize the shape memory/superelastic and mechanical properties of the component. The number, duration and the temperature of the heat treatments may affect the transformation temperatures. Typically, heat treatment temperatures of 400° C. to 550° C. are appropriate to set the final shape and optimize the shape memory and mechanical properties.

The transformation temperatures $M_f$, $M_s$, $R_s'$, $R_f'$, $R_f$, $R_s$, $A_s$, and $A_f$ of the shape memory alloy may be determined using differential scanning calorimetry (DSC) techniques known in the art. DSC measurements may be carried out according to the American Society for Testing and Materials (ASTM) standard F2004-05 entitled "Standard Test Method for Transformation Temperature of Nickel-Titanium Alloys by Thermal Analysis," which is hereby incorporated by reference. Alternatively, methods known as constant load dilatometry and bend and free recovery may be employed to determine the transformation temperatures. Bend and free recovery tests may be carried out in accordance with the ASTM standard F2082-03 entitled "Standard Test Method for Determination of Transformation Temperature of Nickel-Titanium Shape Memory Alloys by Bend and Free Recovery," which is hereby incorporated by reference. Electrical resistivity measurements are also known in the art for determining the phase transformation temperatures of metals and alloys. Such measurements may be carried out by heating and cooling the alloy of interest while recording voltage using a four-probe constant current technique, for example. Using electrical resisitivity measurements, it is possible to characterize phase transformations occurring in the nickel-titanium alloy as a function of applied stress as well as temperature. Diffraction methods, including x-ray, electron and/or neutron diffraction, may also be employed to evaluate the crystal structure of the materials as a function of temperature.

In some cases, DSC testing as provided by the ASTM Standard F2004-05 may be insufficient to fully characterize the phase transformations of shape memory alloys exhibiting an R-phase transformation. For some shape memory alloys, two distinct exothermic peaks are obtained in the data during cooling (the first corresponding to the austenite to R-phase transformation and the second corresponding to the R-phase to martensite transformation), but only a single endothermic valley is obtained during heating. This valley is generally believed to be formed by two overlapping sub-valleys (the first corresponding to the martensite to R-phase transformation and the second corresponding to the R-phase to austenite transformation). However, using the standard DSC test method, it is not possible to isolate and define these overlapped sub-valleys. Accordingly, phase transformation temperatures, in particular $R'_f$ and $A_s$, can only be estimated.

An improved method of characterizing phase transformations in shape memory alloys comprising an R-phase transformation is described in related patent documents, U.S. patent application Ser. No. 12/274,556, published as U.S. Patent Application Publication No. 2009/0139614 and entitled "Method of Characterizing Phase Transformations in Shape Memory Materials," which was filed on Nov. 20, 2008, and is hereby incorporated by reference in its entirety, and also PCT/US2008/085144, which was filed on Dec. 1, 2008. The improved method allows overlapping inflections (e.g., valleys) in DSC or other data to be deconvoluted into sub-inflections (e.g., sub-valleys) that represent distinct phase transformations. Accordingly, the method may allow phase transformation temperatures, such as $A_s$ and $R'_f$, to be unambiguously determined for shape memory alloys having an R-phase transformation.

A loading method for a medical device is described in a related patent document, U.S. patent application Ser. No. 11/950,244 entitled "Method for Loading a Medical Device into a Delivery System," which was filed on Dec. 4, 2007, and is hereby incorporated by reference in its entirety.

EXAMPLES

The inventors have carried out x-ray diffraction experiments in conjunction with tensile testing to obtain graphical and integration data that show evidence of the formation of stress-induced R-phase in a loaded Nitinol test article. The information presented here was gathered using the Stanford Synchrotron Radiation Lightsource (SSRL) housed at the Stanford Linear Accelerator Center (SLAC) in California.

Nitinol test articles that were fully austenitic under zero strain conditions were subjected to a tensile load, and x-ray diffraction data were obtained during loading. The data obtained at strain levels of 0%, 1% and 8% are discussed here. These strain levels are representative of the strain experienced by a self-expanding stent when it is compressed in preparation for delivery into a body vessel and expanded during deployment at a treatment site.

Figure 5:
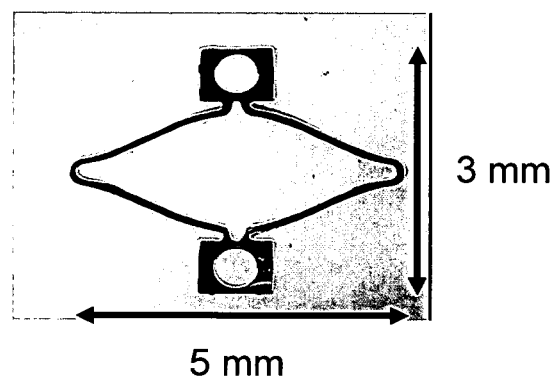
FIG. 5 shows a diamond test article of a two-stage Nitinol alloy.

Diamond-shaped Nitinol samples were employed for the XRD experiments, as shown in FIG. 5. These samples were of the same Nitinol alloy as typical Cook Medical Zilver® self-expanding Nitinol stents. The test articles were laser cut from the same tubing used for Zilver® stents and underwent similar expansion, heat treatment and electro-polishing processes to achieve the final article. The apices of the diamond test articles were designed to match that of typical 7 mm diameter Zilver® stents cut from 1.63 mm Nitinol tubing.

Figure 6A:
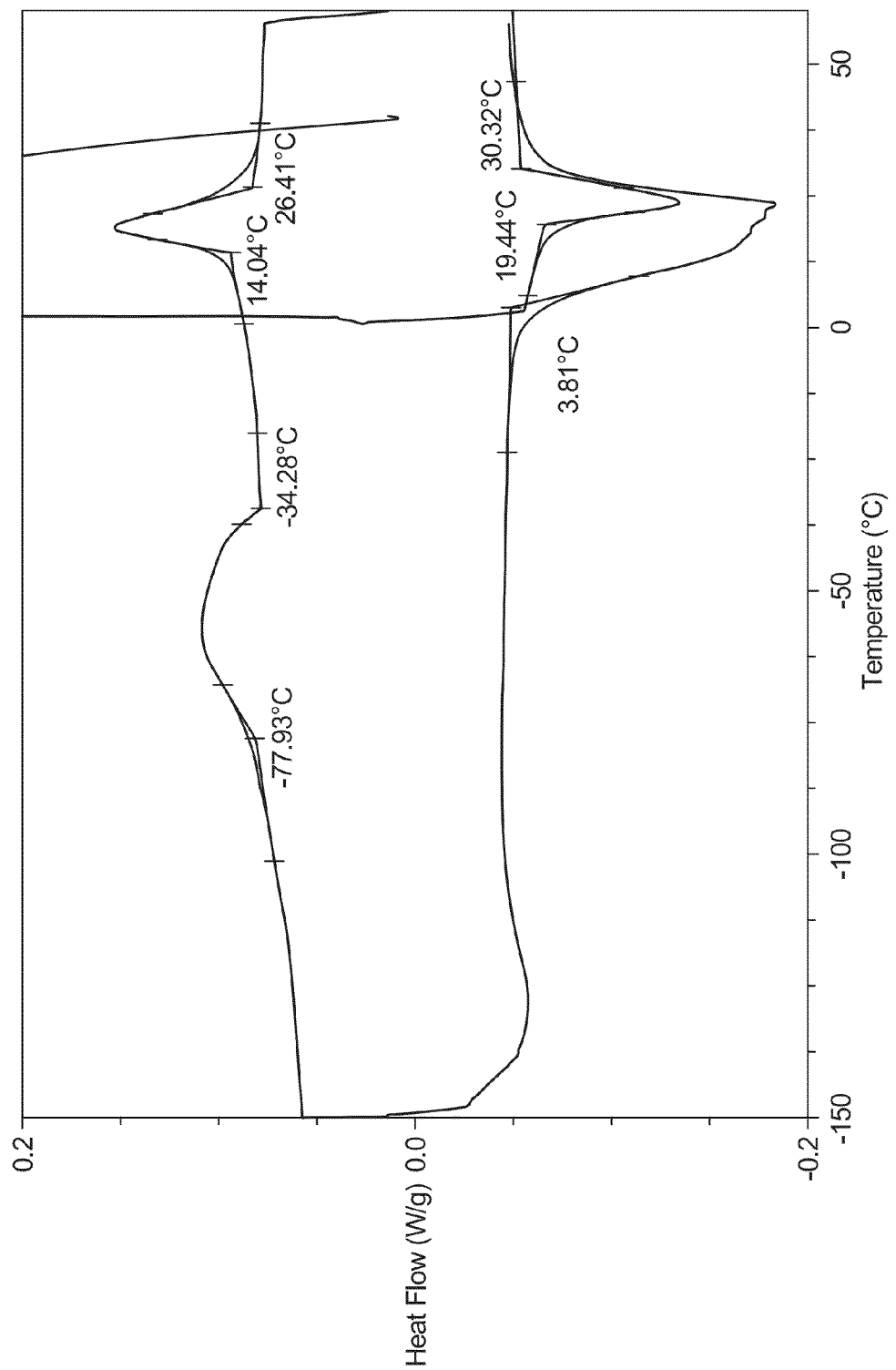
FIG. 6A shows DSC data corresponding to a representative commercial stent.
Figure 6B:
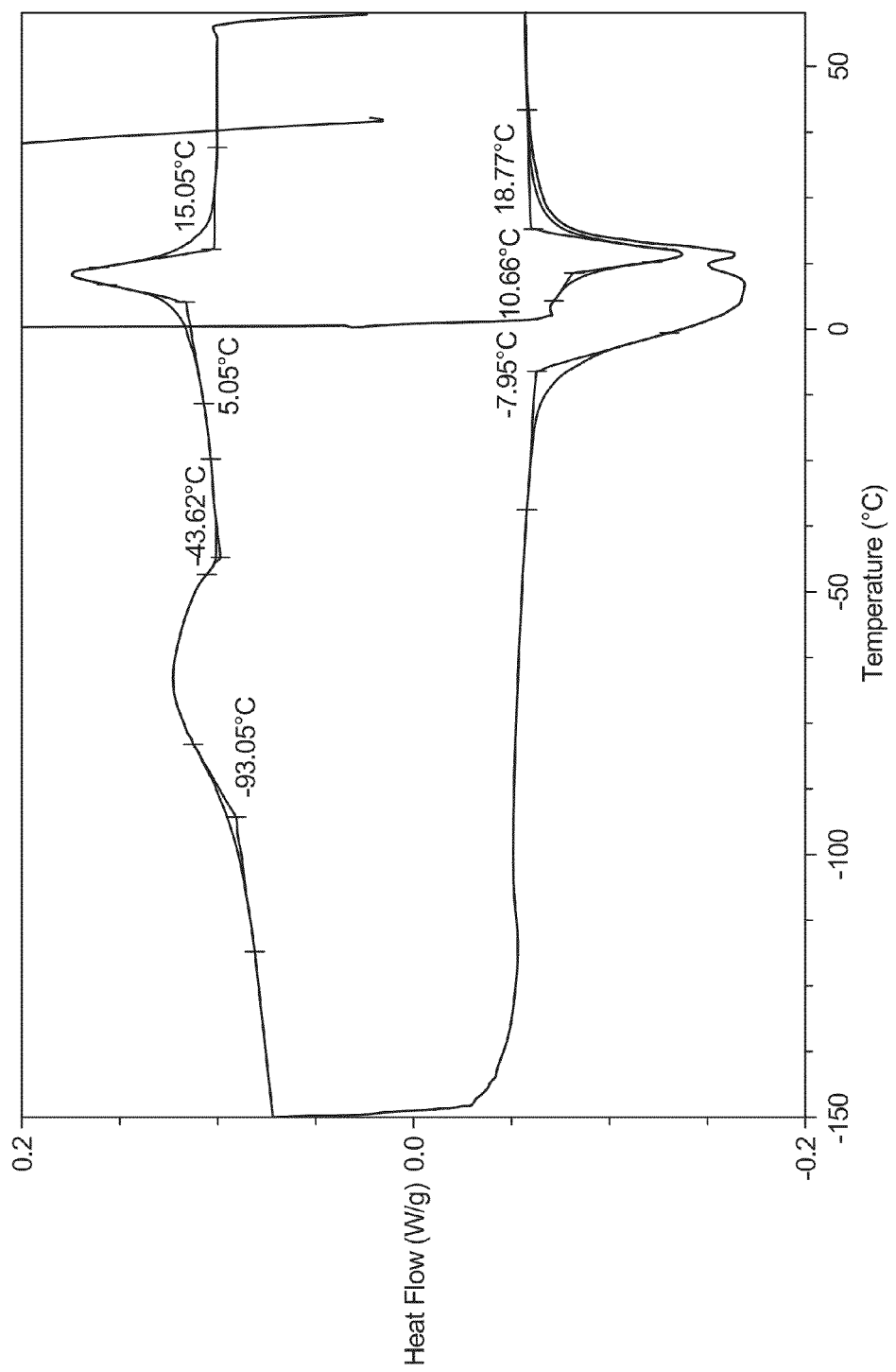
FIG. 6B shows DSC data corresponding to the diamond test article of FIG. 5.

Referring to FIGS. 6A and 6B, DSC testing was performed on the diamond test articles from same lot as those that underwent x-ray diffraction testing. DSC results from the diamond test article (FIG. 6B) showed a comparable DSC landscape to that obtained from a Cook Medical Zilver® stent (FIG. 6A). Both Nitinol alloys are two-stage transformation materials whose transformation temperatures are within ~10° C. of each other.

The diamond test articles were held in a test fixture to facilitate application of a load during the x-ray diffraction tests. The test article was brought to a temperature above the austenite finish temperature of the alloy ($A_f$ as shown by DSC). The initial conditions for the test were temperature≥$A_f$, the test article at no-load. X-ray diffraction data were obtained at the initial conditions. The diamond test article was incrementally deformed by bringing the ends of the sample together, causing the apices to close. X-ray diffraction data were obtained at each deformation increment. The x-ray diffraction testing was performed at locations on the sample where the local stress/strain was expected to be the greatest and then at incrementally higher stresses to achieve sequentially higher and higher strain values.

The data capture method was that of Laue patterns, the characteristic photographic record obtained in the Laue method. The Laue method entails studying crystalline structures by x-ray diffraction, in which a finely collimated beam of polychromatic x-rays falls on a target area whose orientation can be set as desired, and the energy of diffracted beams are recorded on a photographic film via an ion chamber. Laue patterns provide information on the microstructure of the specimen within the target area of the x-ray diffraction beam. The beam is diffracted according to Bragg's law and impinges on an ion chamber of sizable area capturing much of the available diffracted data. The diffracted data is related to the d-spacing of the microstructures (phases) within the target area.

When x-rays are directed in solids they will scatter in predictable patterns based upon the internal structure of the solid. A crystalline solid consists of regularly spaced atoms that can be described by imaginary planes known as crystallographic planes that have particular orientations. The distance between these planes is called the d-spacing for a particular crystallographic direction. The intensity of the diffraction pattern is directly proportional to the number of atoms that are found in the crystallographic planes. Every crystalline solid has a unique pattern of d-spacing (known as the powder pattern), which is a "finger print" for that solid.

Expected d-spacings for a particular microstructure (phase) can be calculated and tabulated to compare to x-ray diffraction data. The major phases expected in the Nitinol test articles at different temperatures are austenite, R-phase and martensite. Other phases include a variety of NiTi precipitates. A feature that may be expected on a Laue pattern corresponding to the R-phase is a doublet that appears as two very discrete rings but very close to each other.

The presence of atoms arranged in planes having particular d-spacings shows up as rings on the pattern. The brighter the ring is, the higher the intensity of that particular crystallographic orientation. Through the use of Area Diffraction Machine software at the SSRL, Laue patterns are generated using this diffracted beam information giving a graphical representation as well as d-spacing identification (using cursor position).

Figure 7A:
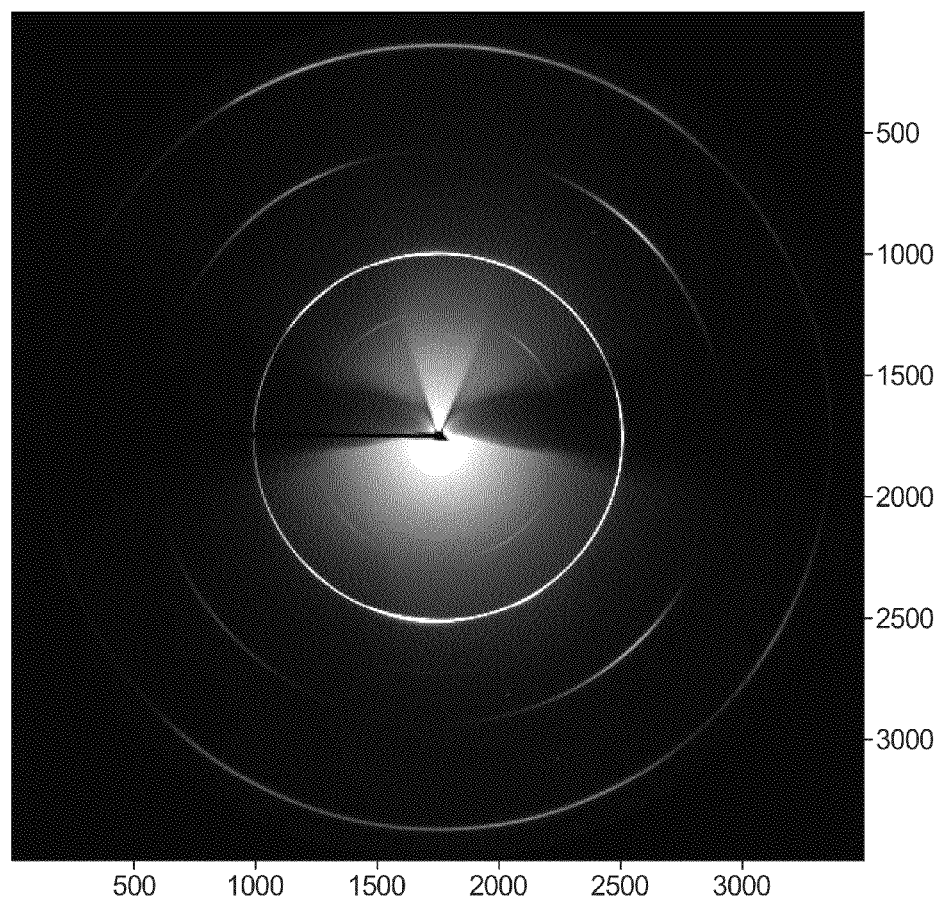
FIG. 7A is a Laue x-ray diffraction pattern obtained from the diamond test article of FIG. 5 under zero strain conditions and at a temperature above $A_f$ for the Nitinol alloy.
Figure 7B:
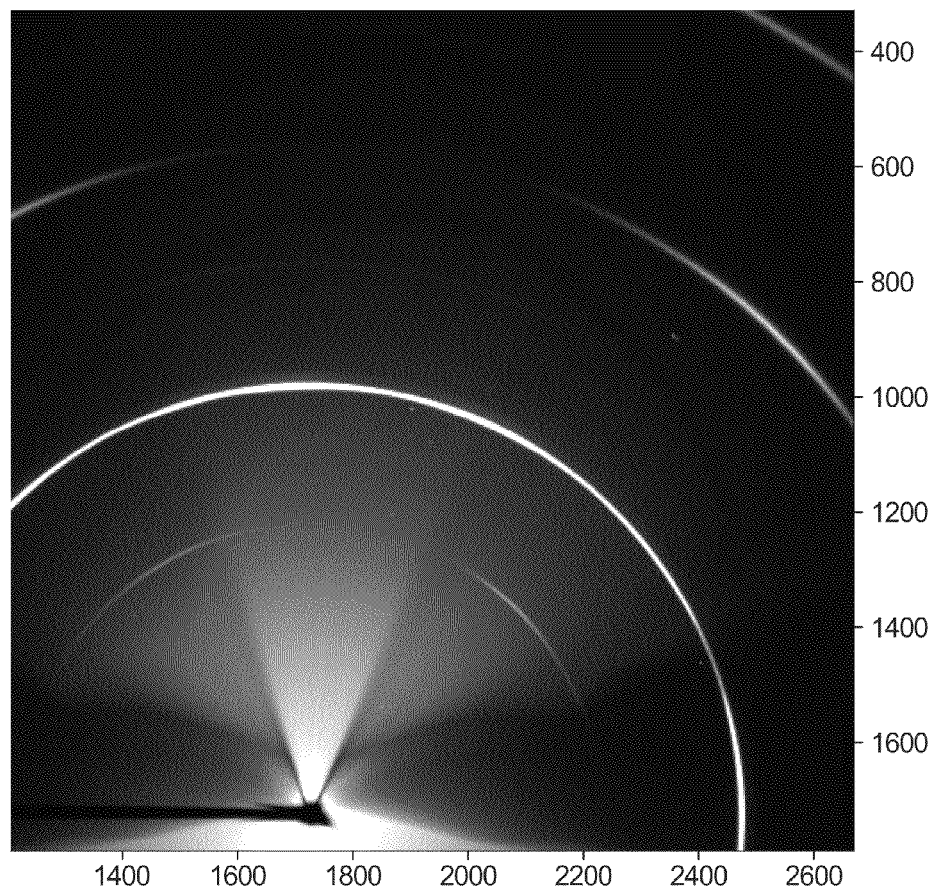
FIG. 7B is a magnified view of FIG. 7A.

At the strain free state, as seen in FIGS. 7A and 7B, the Laue patterns indicate several rings. The d-spacing for these rings have been compared with theoretical or calculated values of typical phases found in Nitinol alloys and indicates that, for established initial conditions, austenite (the most vivid rings in the figure) and NiTi precipitates are present (dim rings in the figure).

Figure 8A:
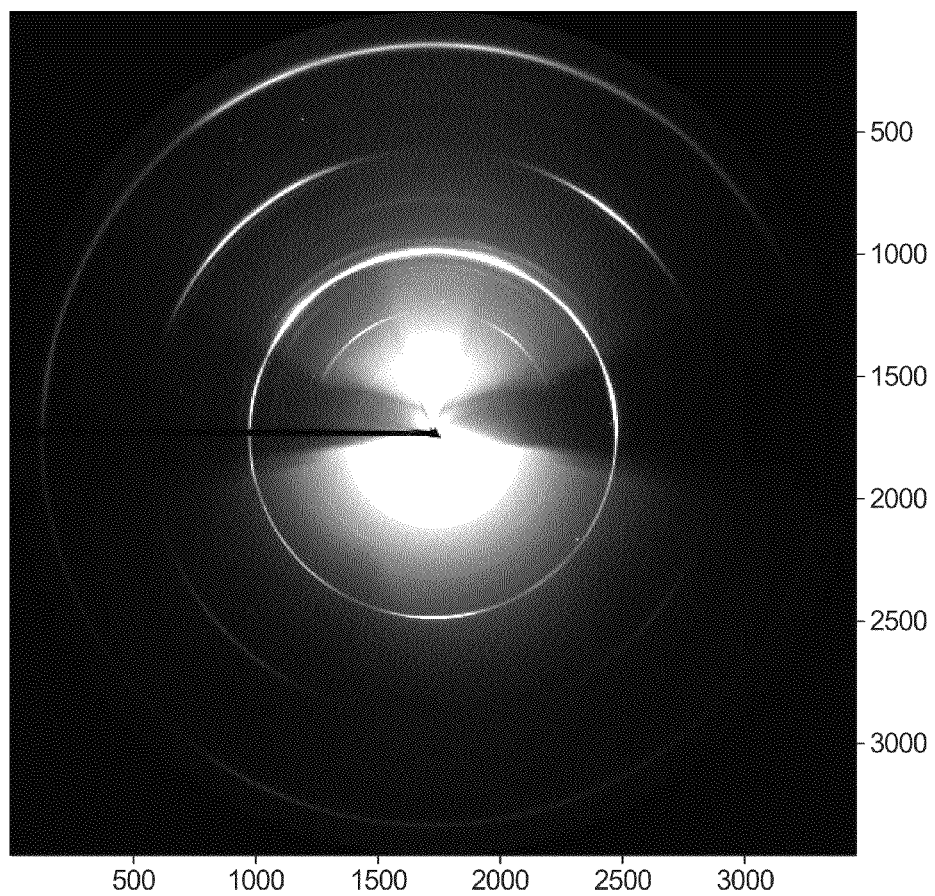
FIG. 8A is a Laue x-ray diffraction pattern obtained from the diamond test article of FIG. 5 under an applied strain of 1% and at a temperature above $A_f$.
Figure 8B:
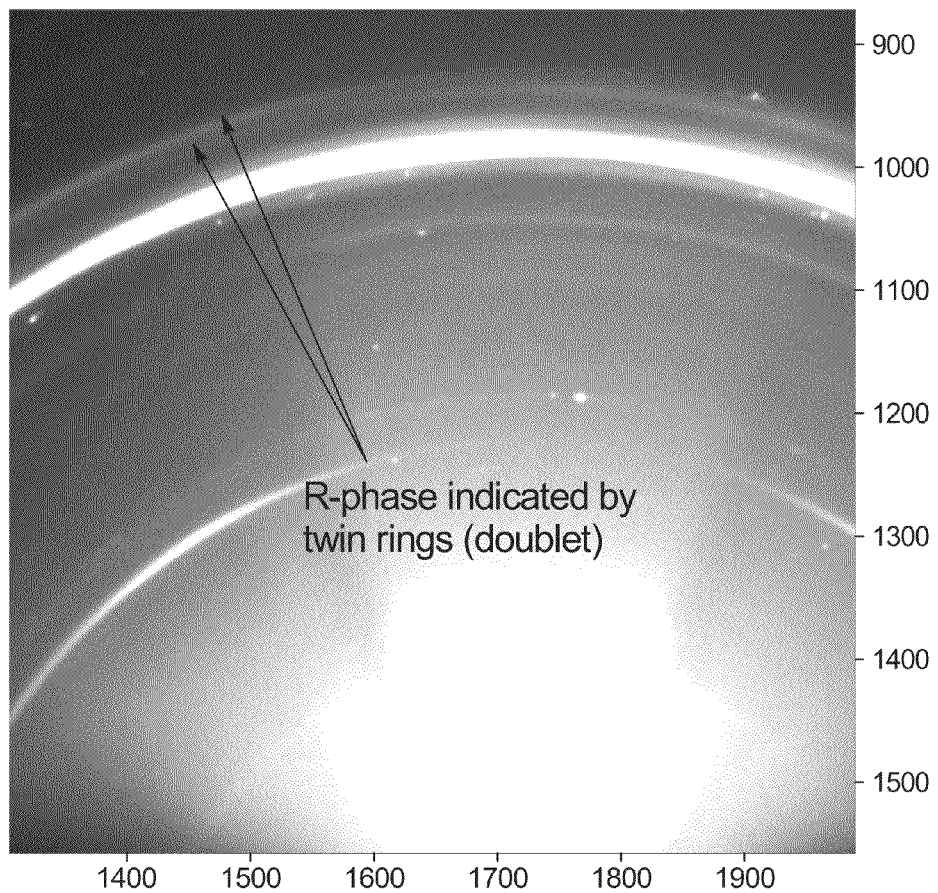
FIGS. 8B-8C are magnified views of FIG. 8A.
Figure 8C:
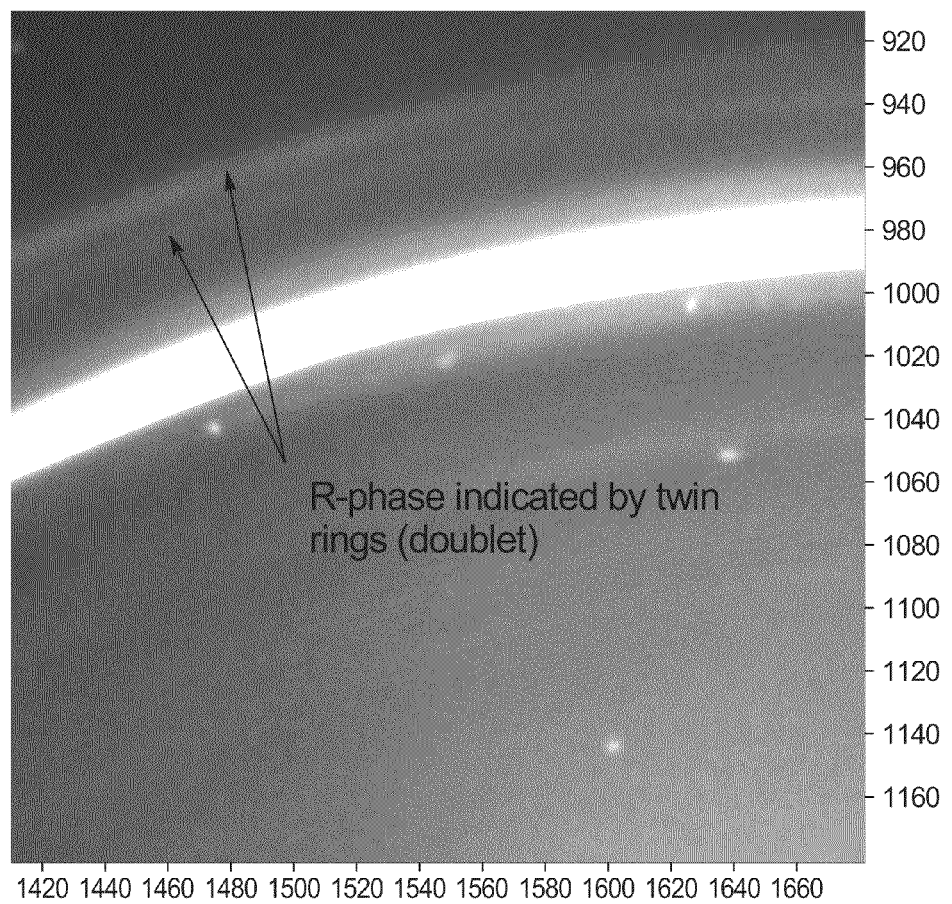
Figure 9A:
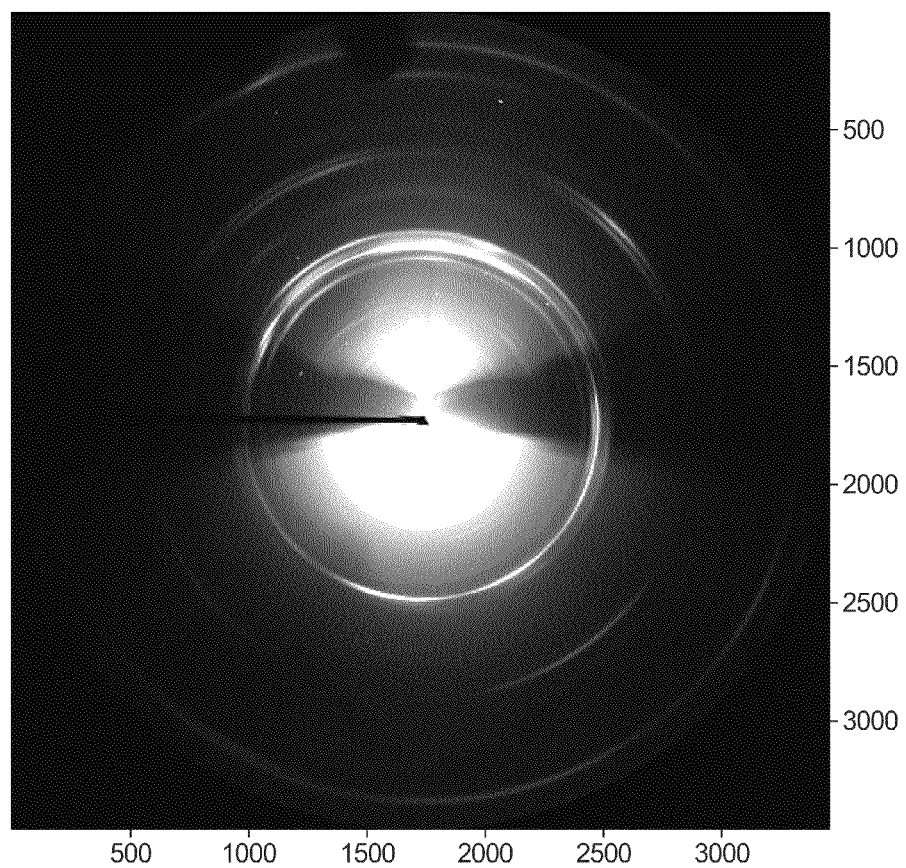
FIG. 9A is a Laue x-ray diffraction pattern obtained from the diamond test article of FIG. 5 under an applied strain of 8% and at a temperature above $A_f$.
Figure 9B:
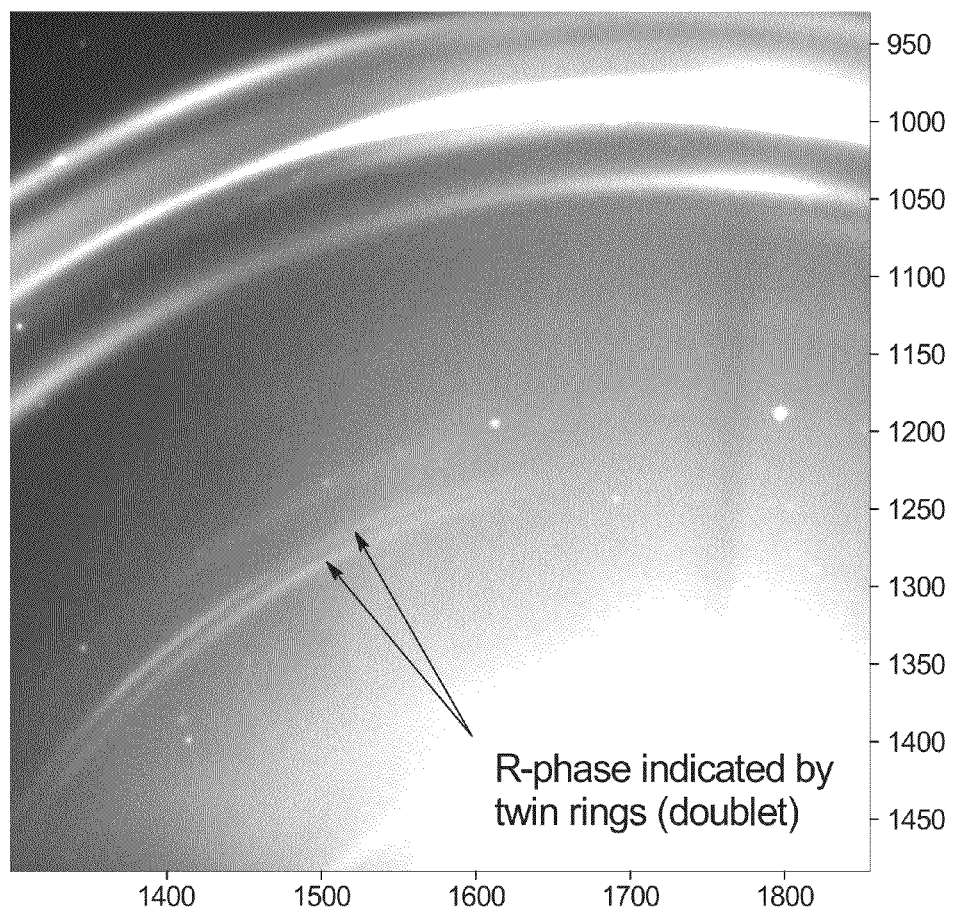
FIGS. 9B-9C are magnified views of FIG. 9A.
Figure 9C:
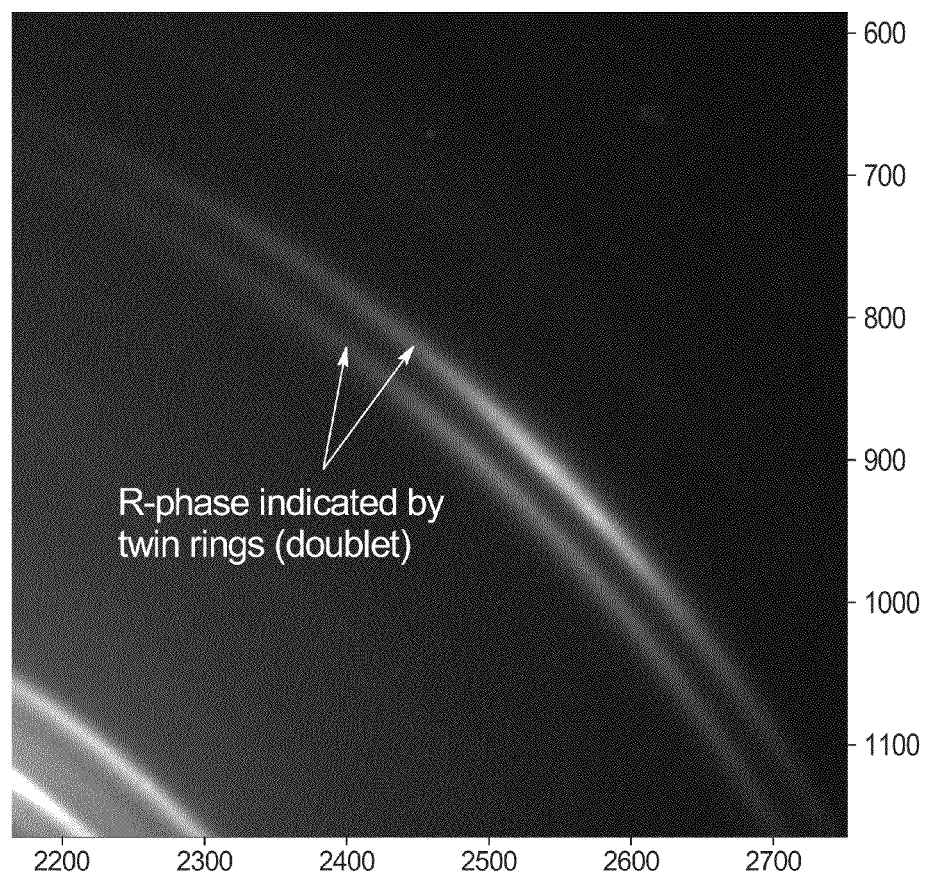

At a strain state of 1%, as seen in FIGS. 8A-8C, more rings appear in the Laue pattern, including a doublet. By comparing the d-spacing of these new rings to the theoretical values, it may be concluded that the R-phase as well as austenite and NiTi precipitates are present. FIGS. 9A-9C are additional Laue patterns obtained under an applied strain of 8%. Arrows in the figures indicate rings that the inventors believe indicate the presence of stress-induced R-phase.

An alternative representation of the crystallographic data may be obtained by integrating the Laue pattern data, as shown for example in FIGS. 10A-10E. The aforementioned software can integrate the Laue pattern data and represent it as intensity peaks on a 2-dimensional plane. The peaks indicate the existence of specific phases with an intensity determined by the crystallography of the specimen. Low intensity or incomplete rings are typically not visible on an integration plot due to the cumulative nature of the integration, thus phases that are less prevalent in the material may not be apparent. Combining the Laue patterns with the integration representations of the x-ray diffraction data, the confidence level concluding the formation of particular phases is improved.

Figure 10A:
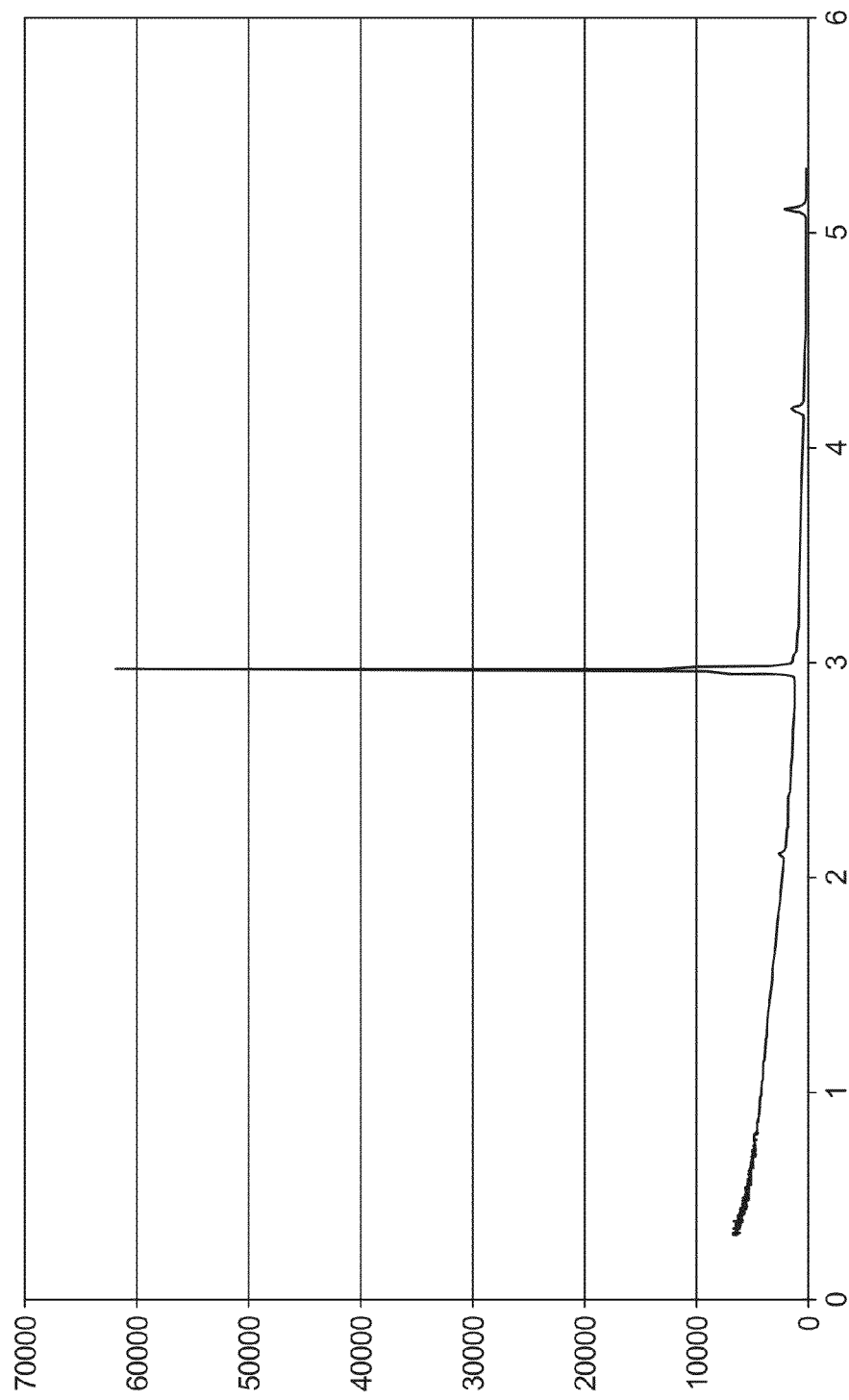
FIG. 10A is an integrated x-ray diffraction pattern obtained from the Laue pattern of FIGS. 7A-7B (at zero applied strain)
Figure 10B:
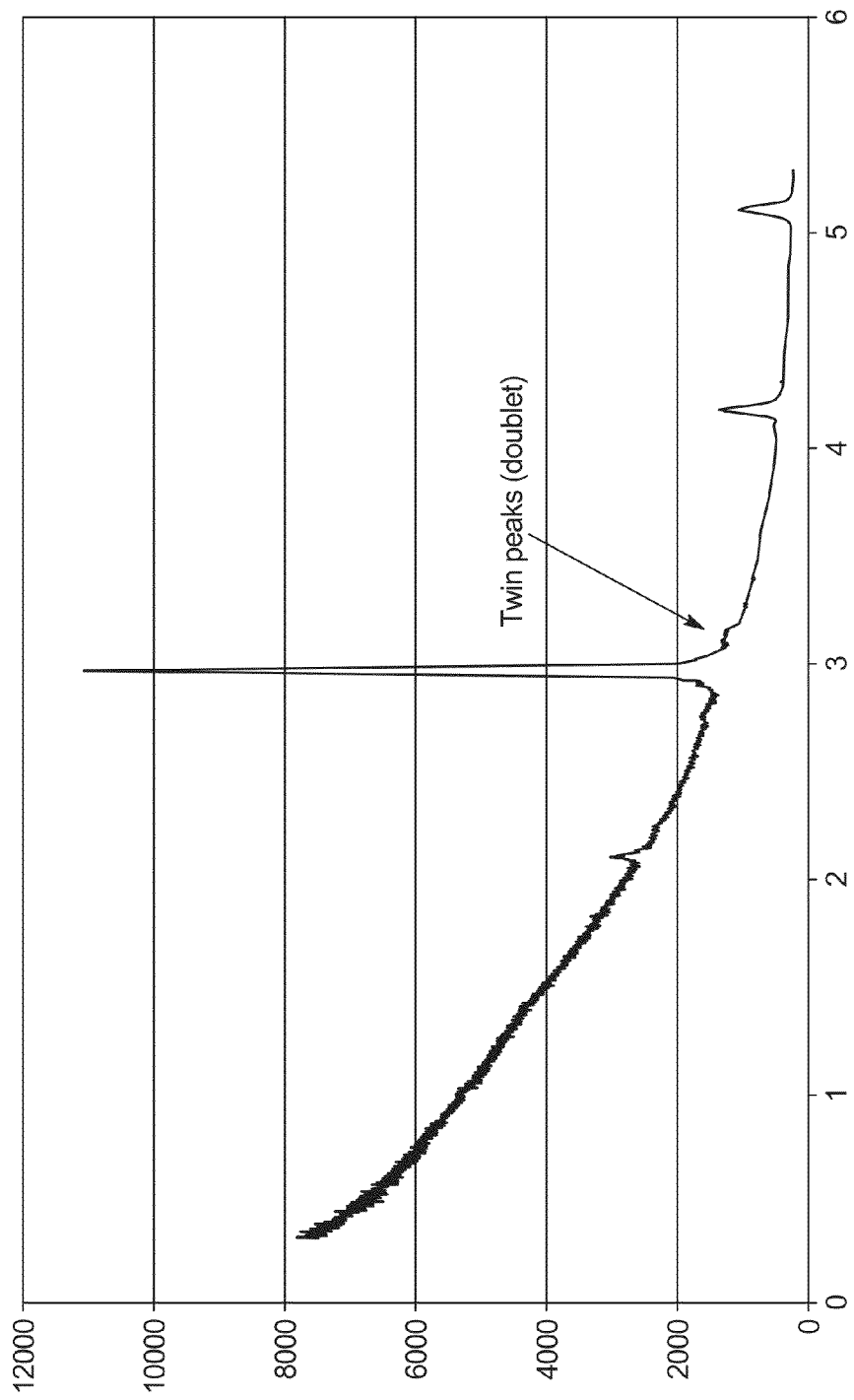
FIGS. 10B-10C are integrated x-ray diffraction patterns obtained from the Laue pattern of FIGS. 8A-8C (at 1% applied strain)
Figure 10C:
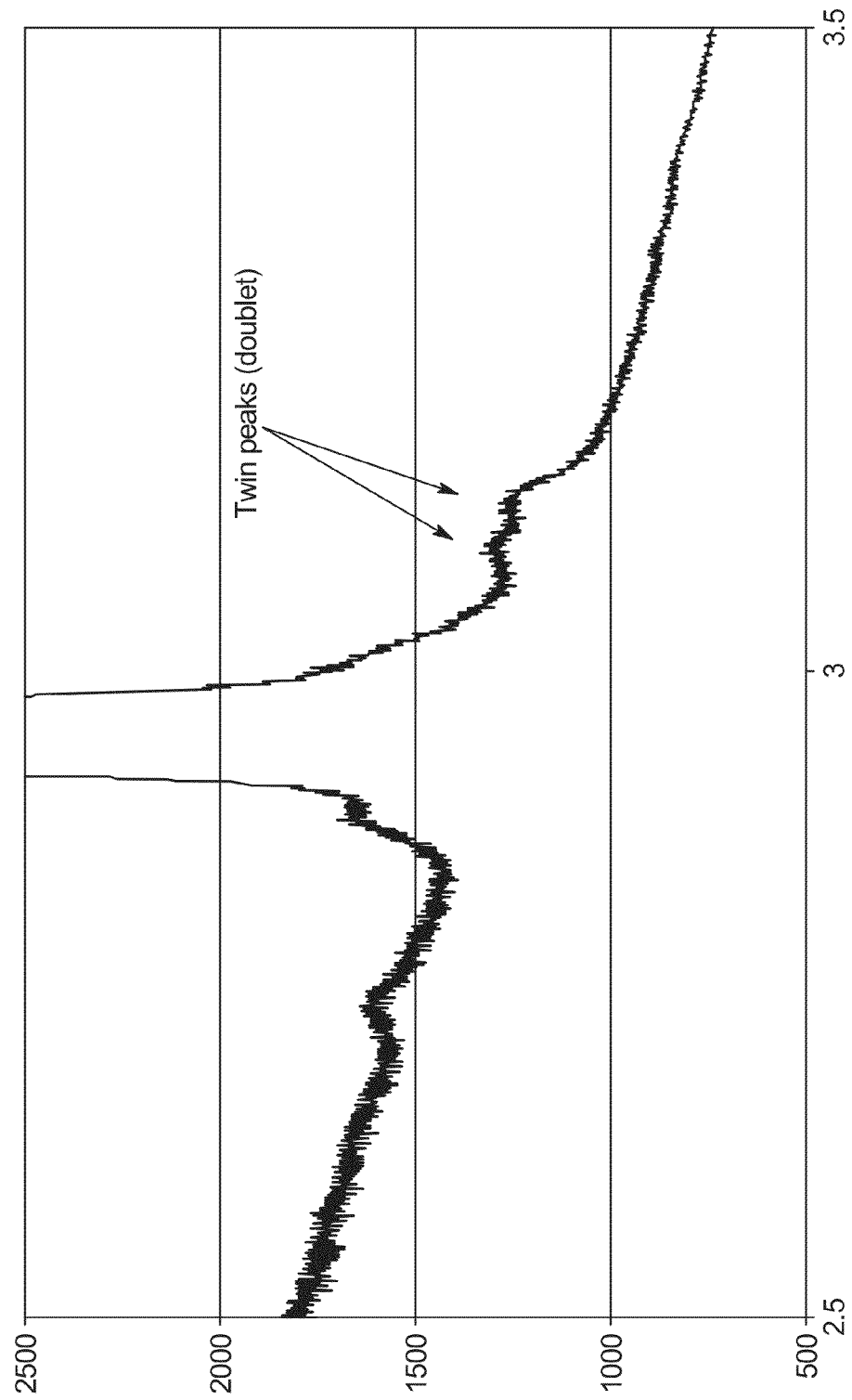
Figure 10D:
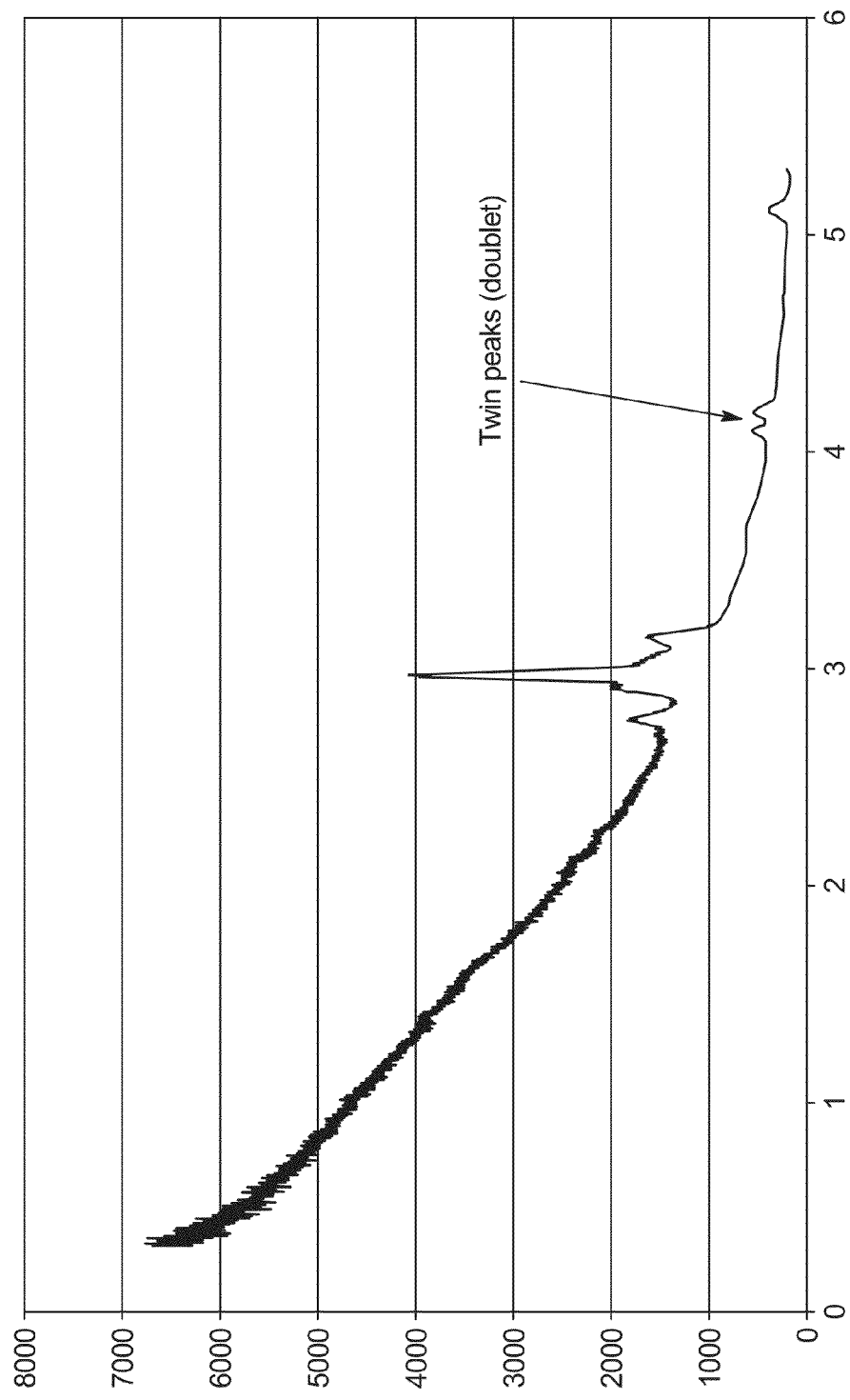
FIGS. 10D-10E are integrated x-ray diffraction patterns obtained from the Laue pattern of FIGS. 9A-9C (at 8% applied strain).
Figure 10E:
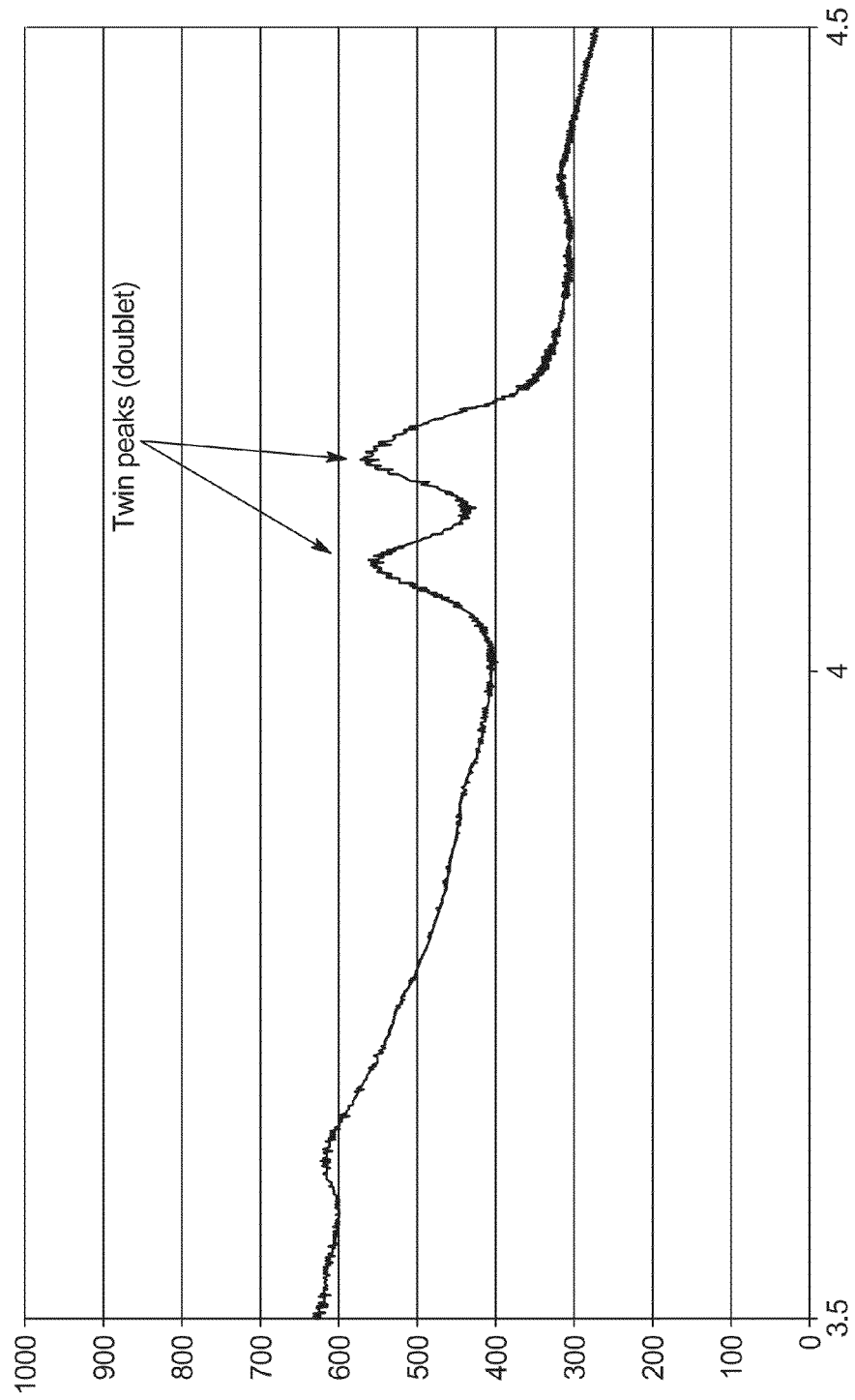

FIG. 10A is an integration of the Laue pattern of FIGS. 7A-7B, which were obtained at zero applied strain; FIGS. 10B-10C are integrations of the Laue pattern of FIGS. 8A-8C, which were obtained at 1% applied strain; and FIGS. 10D-10E are integrations of the Laue pattern of FIGS. 9A-9C, which were obtained at 8% applied strain. Arrows in FIGS. 10B-10E indicate peaks in the diffraction patterns that the inventors believe correspond to stress-induced R-phase.

In summary, it appears that while holding all parameters constant except for stress, which effects a strain within the material, R-phase can be seen forming as strain levels increase beyond no load conditions. This has come to be known as stress induced R-phase (SIR).

A method of loading a medical device comprising a two-stage shape memory alloy into a delivery system that involves an R-phase transformation has been described herein. Also described is a delivery system including the medical device. The inventors have recognized that the R-phase of a two-stage shape memory alloy, which is generally avoided or ignored in the medical device community, may provide advantages for medical devices.

Although the present invention has been described in considerable detail with reference to certain embodiments thereof, other embodiments are possible without departing from the present invention. The scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A method of loading a medical device into a delivery system, the method comprising:
    providing a medical device comprising a two-stage shape memory alloy at a temperature at which at least a portion of the alloy is austenite;
    applying a stress to the medical device at the temperature, the stress being sufficient to form R-phase from at least a portion of the austenite and not exceeding 200 MPa;
    obtaining a delivery configuration of the medical device; and
    loading the medical device in the delivery configuration into a restraining member, wherein the delivery configuration comprises stress-induced R-phase.

2. The method of claim 1 wherein the stress applied to the medical device is not sufficient to form martensite from the R-phase.

3. The method of claim 2 wherein the delivery configuration does not include stress-induced martensite.

4. The method of claim 1 wherein the stress-induced R-phase is present in the delivery configuration of the medical device in regions of maximum strain.

5. The method of claim 1 wherein the stress applied to the medical device is sufficient to form martensite from at least a portion of the R-phase.

6. The method of claim 5 wherein the delivery configuration of the medical device further comprises stress-induced martensite.

7. The method of claim 1 wherein the temperature is between about $A_s$ and $A_s+10°$ C. of the shape memory alloy.

8. The method of claim 1 wherein the temperature is at or above $A_f$ of the shape memory alloy, the alloy being fully austenitic at the temperature.

9. The method of claim 1 further comprising, prior to applying the stress to the medical device, processing the shape memory alloy to maximize a difference between a martensite start temperature and an R-phase start temperature of the alloy.

10. The method of claim 1 wherein applying the stress to the medical device comprises radially compressing the medical device and wherein the medical device is a self-expanding stent.

11. A method of loading a medical device into a delivery system, the method comprising:
    providing a medical device comprising a two-stage shape memory alloy, the alloy being at a temperature at which the alloy includes a parent phase, the parent phase not being R-phase;
    applying a stress of no more than 200 MPa to stress-induce the R-phase from the parent phase in at least a portion of the alloy at the temperature;
    obtaining a delivery configuration of the medical device; and
    loading the medical device in the delivery configuration into a restraining member, wherein the delivery configuration comprises stress-induced R-phase.

12. The method of claim 11, wherein the parent phase is austenite.

13. The method of claim 11, wherein the parent phase is martensite.

14. The method of claim 11, further comprising stress-inducing martensite from at least a portion of the stress-induced R-phase.

15. The method of claim 11, wherein the delivery configuration of the medical device further comprises stress-induced martensite.

16. The method of claim 11 further comprising, prior to applying the stress to the medical device, processing the shape memory alloy to maximize a difference between a martensite start temperature and an R-phase start temperature of the alloy.

17. A method of loading a medical device into a delivery system, the method comprising:
    providing a medical device comprising a two-stage shape memory alloy at a temperature at which at least a portion of the alloy is austenite;
    applying a stress to the medical device at the temperature, the stress being sufficient to form R-phase from at least a portion of the austenite;
    obtaining a delivery configuration of the medical device; and
    loading the medical device in the delivery configuration into a restraining member, wherein the delivery configuration comprises stress-induced R-phase,
    wherein, prior to applying the stress to the medical device, the shape memory alloy is processed to maximize a difference between a martensite start temperature and an R-phase start temperature of the shape memory alloy.

18. A method of loading a medical device into a delivery system, the method comprising:
    providing a medical device comprising a two-stage shape memory alloy, the alloy being at a temperature at which the alloy includes a parent phase, the parent phase not being R-phase;
    stress-inducing the R-phase from the parent phase in at least a portion of the alloy at the temperature;
    obtaining a delivery configuration of the medical device; and
    loading the medical device in the delivery configuration into a restraining member, wherein the delivery configuration comprises stress-induced R-phase,
    wherein, prior to stress-inducing the R-phase, the shape memory alloy is processed to maximize a difference between a martensite start temperature and an R-phase start temperature of the shape memory alloy.

* * * * *